(12) United States Patent
Wang et al.

(10) Patent No.: US 6,900,013 B1
(45) Date of Patent: May 31, 2005

(54) METHODS AND COMPOSITIONS FOR IDENTIFYING NUCLEIC ACID MOLECULES USING NUCLEOLYTIC ACTIVITIES AND HYBRIDIZATION

(75) Inventors: Guoqing Wang, Yi Wu (CN); Lei Wu, San Diego, CA (US); Xiaobo Wang, San Diego, CA (US); Jing Cheng, Beijing (CN); WeiPing Yang, San Diego, CA (US)

(73) Assignee: AVIVA Biosciences Corporation, San Diego, CA (US)

( * ) Notice: Subject to any disclaimer, the term of this patent is extended or adjusted under 35 U.S.C. 154(b) by 0 days.

(21) Appl. No.: 09/648,081

(22) Filed: Aug. 25, 2000

(51) Int. Cl.[7] .......................... C12Q 1/68; C12P 19/34; C12M 1/34; C07H 21/02; C07H 21/04

(52) U.S. Cl. ..................... 435/6; 435/91.1; 435/91.2; 435/287.2; 536/23.1; 536/24.3; 536/24.33

(58) Field of Search .................... 435/6, 91.1, 91.51, 435/7.5, 183, 287.2; 436/94; 536/23.1, 24.3, 24.33, 25.3, 25.32, 25.4

(56) References Cited

U.S. PATENT DOCUMENTS

| 3,687,808 A | 8/1972 | Merigan, Jr. et al. |
| 5,143,854 A | 9/1992 | Pirrung et al. |
| 5,242,974 A | 9/1993 | Holmes |

(Continued)

FOREIGN PATENT DOCUMENTS

| WO | WO 95/21944 | 8/1995 |
| WO | WO 99/32663 | 7/1999 |
| WO | WO 00/34521 | 6/2000 |

OTHER PUBLICATIONS

Tyagi et al., Molecular beacons: probes that fluoresce upon hybridization. Nature Biotechnology 14, 303–308, Mar. 1996.*
Alizah et al., Nature, 403:503–511 (2000).
Arribas et al., Clin. Cancer Res., 5:3454–3459 (1999).

(Continued)

Primary Examiner—Ethan Whisenant
Assistant Examiner—Frank Lu
(74) Attorney, Agent, or Firm—David R Preston & Associates APC; Elizabeth Orr

(57) ABSTRACT

The present invention recognizes that identifying genes expressed during developmental processes, stress responses, and disease states can advance understanding of these biological functions, and can contribute to identifying targets for therapeutic drugs. In addition, the present invention recognizes that rapid and reliable profiling of genetic variations, such as mutations and SNPs, is of increasing importance to diagnostics, prognostics, forensics, heredity determinations, and pharmacogenetics. One aspect of the present invention provides a method of identifying one or more nucleic acid molecules that are expressed under a given set of conditions based on their complementarity to known sequences, or one or more mutations or SNPs in a population of nucleic acid molecules. The method includes: contacting at least one probe nucleic acid molecule with a survey population of nucleic acid molecules under conditions that promote nucleic acid hybridization to generate a probe-survey population mixture of nucleic acid molecules, treating the probe-survey population mixture of nucleic acid molecules with a nucleolytic activity, such that nucleolytic activity-sensitive nucleic acid molecules are digested, and contacting the resulting mixture of nucleolytic activity-protected nucleic acid molecules with a solid support comprising one or more attached nucleic acid molecules to generate attached nucleic acid molecule/nucleolytic activity-protected nucleic acid molecule complexes, and identifying one or more of the attached nucleic acid molecules or one or more of the nucleolytic activity-protected nucleic acid molecules in one or more attached nucleic acid molecule/nucleolytic activity-protected nucleic acid molecule complexes.

32 Claims, 11 Drawing Sheets

U.S. PATENT DOCUMENTS

| | | | |
|---|---|---|---|
| 5,359,115 | A | 10/1994 | Campbell et al. |
| 5,384,261 | A | 1/1995 | Winkler et al. |
| 5,405,783 | A | 4/1995 | Pirrung et al. |
| 5,412,087 | A | 5/1995 | McGall et al. |
| 5,420,328 | A | 5/1995 | Campbell |
| 5,424,186 | A | 6/1995 | Fodor et al. |
| 5,429,807 | A | 7/1995 | Matson et al. |
| 5,436,327 | A | 7/1995 | Southern et al. |
| 5,445,934 | A | 8/1995 | Fodor et al. |
| 5,472,672 | A | 12/1995 | Brennan |
| 5,527,681 | A | 6/1996 | Holmes |
| 5,529,756 | A | 6/1996 | Brennan |
| 5,532,128 | A | 7/1996 | Eggers et al. |
| 5,545,531 | A | 8/1996 | Rava et al. |
| 5,554,501 | A | 9/1996 | Coassin et al. |
| 5,556,752 | A | 9/1996 | Lockhart et al. |
| 5,561,071 | A | 10/1996 | Hollenberg et al. |
| 5,571,639 | A | 11/1996 | Hubbell et al. |
| 5,593,839 | A | 1/1997 | Hubbell et al. |
| 5,599,695 | A | 2/1997 | Pease et al. |
| 5,624,711 | A | 4/1997 | Sundberg et al. |
| 5,629,156 | A * | 5/1997 | Shah et al. ............... 435/6 |
| 5,658,734 | A | 8/1997 | Brock et al. |
| 5,681,943 | A | 10/1997 | Letsinger et al. |
| 5,700,637 | A | 12/1997 | Southern |
| 5,770,370 | A | 6/1998 | Kumar |
| 5,773,257 | A * | 6/1998 | Nielson et al. ............ 435/91.1 |
| 5,888,819 | A | 3/1999 | Goelet et al. |
| 5,952,174 | A | 9/1999 | Nikiforov et al. |
| 5,994,076 | A | 11/1999 | Chenchik et al. |
| 5,994,079 | A | 11/1999 | De La Rosa et al. |
| 5,998,136 | A | 12/1999 | Kamb |
| 6,004,744 | A | 12/1999 | Goelet et al. |
| 6,004,752 | A | 12/1999 | Loewy et al. |
| 6,004,755 | A | 12/1999 | Wang |
| 6,013,431 | A | 1/2000 | Soderlund et al. |
| 6,228,580 | B1 | 4/2001 | Blumenfeld et al. |
| 6,232,066 | B1 * | 5/2001 | Felder et al. .............. 435/6 |
| 6,238,869 | B1 * | 5/2001 | Kris et al. ................ 435/6 |
| 6,268,146 | B1 | 7/2001 | Shultz et al. |
| 6,448,010 | B1 * | 9/2002 | Zhao ........................ 435/6 |
| 6,458,533 | B1 | 10/2002 | Felder et al. |
| 2003/0096232 | A1 | 5/2003 | Kris et al. |

OTHER PUBLICATIONS

Beaucage and Iyer, Tetrahedron, 48:2223–2311 (1992).
Beaucage and Iyer, Tetrahedron, 49:6123–6194 (1993).
Debouck and Goodfellow, Nature Genetics Supple., 21:48–50 (1999).
Duggan et al., Nature Genetics Supple, 21:10–14 (1999).
Englisch et al., Angewandte Chemie., International Edition, 30:613–629 (1991).
Gerhold et al., Trends Biochem. Sci., 24:168–173 (1999).
Haines and Gillispie, Biotechniques, 12:736–741 (1992).
Lau et al., Anal. Biochem., 209:360–366 (1993).
Martin, Helv. Chim. Acta, 78:486–504 (1995).
Pollack et al., Nature Genetics, 23:41–46 (1999).
Rosenthal and Jones, Nucleic Acids Res., 18:3095–3096 (1990).
Schena et al., Science, 270:467–470 (1995).
Sinha and Cook, Nucleic Acids Res., 16:2659–2669 (1988).
Smith et al., Nucleic Acids Res.,13:2399–2412 (1985).
Strauss and Jacobowitz, Brain Res. Mol. Brain Res., 20:229–239 (1993).
Tanner et al., Clin. Cancer Res., 1:1455–1461 (1995).
Thiesen et al., Tetrahedron Letters, 33:5033–5036 (1992).
Walmsley and Patient, Mol. Biotechnol., 1:265–275 (1994).
Nikiforv et al., Nucleic Acid Research, 22:20:4167–4175 (1994).
Liu, et al., Nature, 403:175–79 (2000).
Surryr, Xenobiotica, 29(8):827–36 (1999) (Abstract).
Cheung and Nelson, Genomics, 47:1–6 (1998).
Pease et al., Proc. Natl. Acad. Sci., 91:5022–5026 (1994).
Tyagi et al., Nature Biotechnol., 14:300–307 (1996).

* cited by examiner

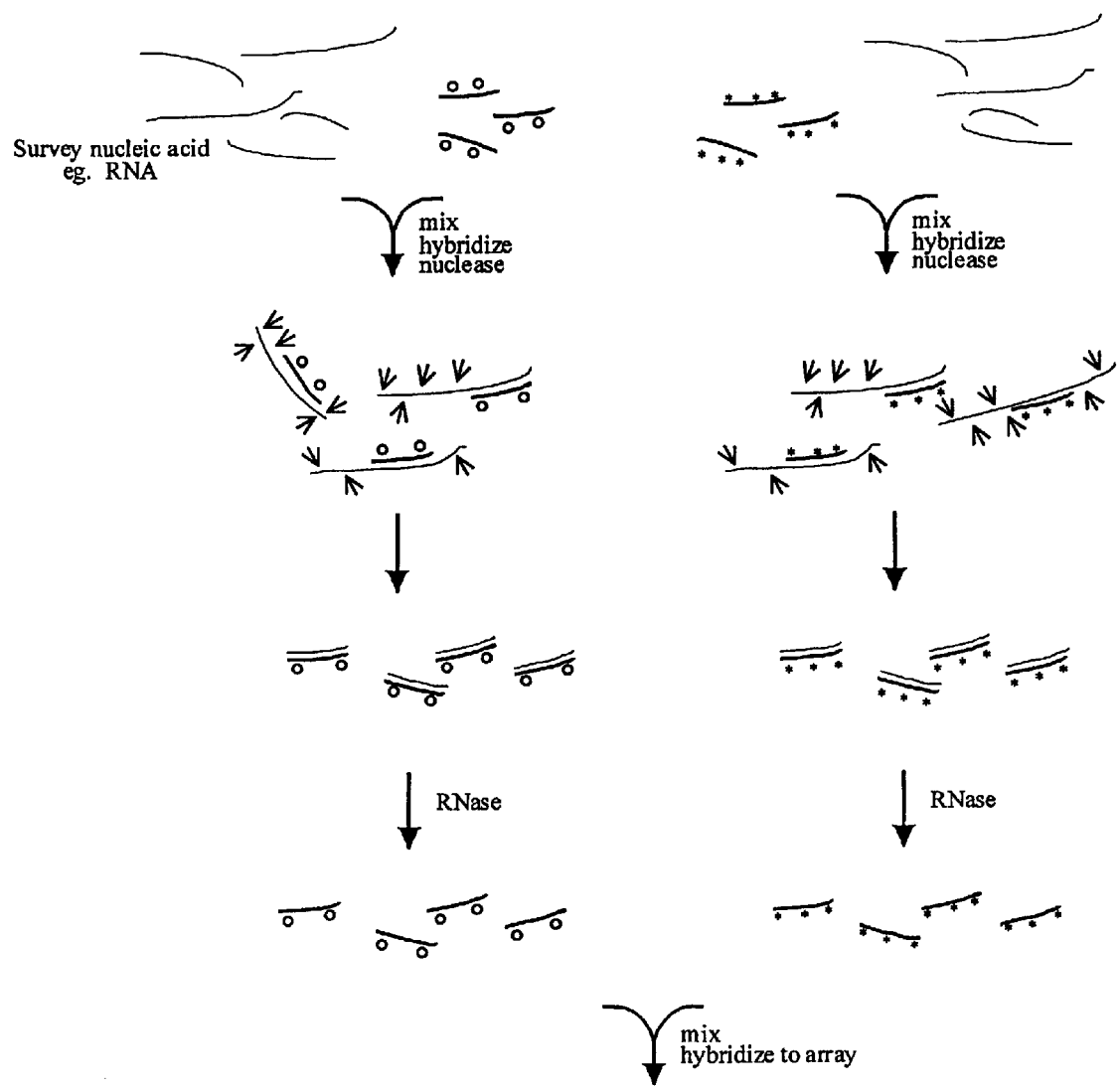
FIG. 3
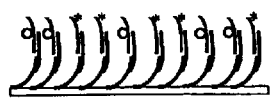

SEQUENCE LISTING

```
<160> NUMBER OF SEQ ID NOS:  8

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Artificial
      sequences used in the examples section

<400> SEQUENCE: 1
catgttgggt ggttgtccaa aagagcgtgc agagatt                                   37

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Artificial
      sequences used in the examples section

<400> SEQUENCE: 2
aatctctgca cgctcttttg gacaa                                                25

<210> SEQ ID NO 3
```

```
<211> LENGTH: 45
<212> TYPE: DNA
<213> ORGANISM: Artificial Sequence
<220> FEATURE:
<223> OTHER INFORMATION: Description of Artificial Sequence: Artificial
      sequences used in the examples section

<400> SEQUENCE: 3
aatctctgca cgctcttttg gacaaccacc caacatgttg tgctt              45

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Artificial
      sequences used in the examples section

<400> SEQUENCE: 4
catgttgggt ggttgtccaa aagagcgtgc agagatt                       37

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Artificial
      sequences used in the examples section

<400> SEQUENCE: 5
aatctctgca cgctcttttg gacaa                                    25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Artificial
      sequences used in the examples section

<400> SEQUENCE: 6
aatctctgca cgctcttttg gacac                                    25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Artificial
      sequences used in the examples section

<400> SEQUENCE: 7
aatctctgca cgctcttttg gacag                                    25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Artificial
      sequences used in the examples section

<400> SEQUENCE: 8
aatctctgca cgctcttttg gacat                                    25
```

US 6,900,013 B1

METHODS AND COMPOSITIONS FOR IDENTIFYING NUCLEIC ACID MOLECULES USING NUCLEOLYTIC ACTIVITIES AND HYBRIDIZATION

The present application claims benefit of priority to patent application Ser. No. 10/355,411 entitled "Methods and Compositions for Identifying Nucleic Acid Molecules Using Nucleolytic Activities and Hybridization" filed in The People's Republic of China on Aug. 18, 2000, docket number 12000712cb which is incorporated by reference herein in its entirety.

TECHNICAL FIELD

The invention relates to the field of identifying nucleic acid molecules using nucleic acid hybridization techniques. More specifically, it relates to the use of nucleolytic activities to select for nucleic acids that are complementary to sequences of interest and that can be identified using hybridization techniques.

BACKGROUND

The identification of nucleic acids by their sequence is important to the study of gene expression and regulation, to epidemiology and public health, to diagnostics and prognostics, to heredity determination (such as paternity determination), and to forensics. The ability of one strand of a nucleic acid molecule to hybridize to a complementary stand of another nucleic acid molecule allows for the capture of nucleic acid molecules of interest from a population of nucleic acid molecules that may be large and complex. Such capture can lead to the identification and/or purification of nucleic acid molecules of interest in complex populations of nucleic acid molecules, such as the DNA making up the genome of a human being or the population of RNA molecules that are expressed by a cell under certain conditions, for example, a disease state.

Analysis of the expression of RNA transcripts by electrophoresis, blotting to membranes, and hybridization of labeled probes ("Northern blots") can provide quantitative data on the expression of genes. However, this method of analysis is labor-intensive and time consuming. In addition, the sensitivity of this method is relatively low, and it is impractical for analyzing the expression of many different genes, as hybridization with each additional probe corresponding to a different gene requires a round of stripping the old probe from the membrane, hybridizing the new probe, washing the membrane, and audoradiography for signal detection.

RNase protection assays allow for increased sensitivity, more reliable quantitation, and the analysis of multiple RNA transcripts in a single hybridization reaction. However, the number of genes that can be analyzed in one reaction is still relatively low, and gel electrophoresis and autoradiography are required, which are labor and time-consuming.

Nucleic acid chips or arrays allow for the identification of a large set of nucleic acid molecules simultaneously (see, for example, Debouck and Goodfellow (1999) Nature Genetics Suppl., 21: 48–50; Duggan, et al. (1999) Nature Genetics Suppl., 21: 10–14; Gerhold et al. (1999) Trends Biochem Sci. 24: 168–173; Alizadeh et al., Nature 403: 503–5110). When applied to the study of gene expression, the use of gene chips or arrays can rapidly identify a set of genes expressed under given conditions. Such methods typically involve hybridizing cDNA synthesized from RNA by reverse transcription to a DNA array that has sequences from many genes attached to it in an ordered pattern. The cDNA is labeled by incorporation of labeled nucleotides during synthesis (see, for example, Schena et al. (1995) Science 270: 467–470), or in some cases by the incorporation of labeled primers (U. S. Pat. No. 6,004,755 issued Dec. 21, 1999 to Wang). However, the efficiency of reverse transcription can vary among different RNA transcripts, such that the incorporation of label may be quite variable. Variable rates of reverse transcription can also lead to under or overrepresentation of particular cDNAs with respect to the original RNA transcript population. Another difficulty is that cDNAs synthesized by reverse transcription of RNA transcripts will hybridize with different efficiencies to nucleic acids on solid supports, due to the variability of their lengths. Thus it is difficult to obtain accurate data on the levels of expression of genes in a population. This is particularly problematic when comparing two populations of RNA, in which the two populations may be standardized with respect to levels of expression of a particular message.

Mutations are alterations in the genome with respect to the standard wild-type sequence. Mutations can be deletions, insertions, or rearrangements of nucleic acid sequences at a position in the genome, or they can be single base changes at a position in the genome, referred to as "point mutations". Mutations can be inherited, or they can occur in certain cells during the lifespan of an individual. Particular mutations can be correlated with certain cancers, or with the degree of malignancy of certain cancers.

Single nucleotide polymorphisms (SNPs) are positions of variablilty in the genome due to a single base change with respect to the wild type sequence. In some cases, SNPs are point mutations that are diagnostic of genetic defects, for example sickle cell anemia. SNPs can also be positions in the genome where some degree of variability is expected among a population, such as a human population. SNPs can correlate with the ability of a patient to respond positively or negatively to one or more drugs or medications, and thus their identification can be useful in pharmacogenetics. Identifying the nucleotides at particular SNP sites can also be used to identify an individual with a high degree of reliability, and thus can have value in heredity determinations, criminology, and forensics.

While point mutations and SNPs can have profound consequences on the health of an individual and provide a highly reliable tool for identifying an individual, they are somewhat difficult to detect. There are currently several variations on methods of detecting mutations and SNPs on DNA arrays. These methods rely on amplifying a subject's DNA prior to hybridization and identification on the chip. Amplification methods can result in misincorporated bases that can provide inaccurate information on the identity of bases at known or suspected mutation or SNP sites. Moreover, in many cases it is important to identify mutations or SNPs in genes that are expressed, and many genes may not be expressed in a given tissue at a particular time. It is also desirable to identify genes or regions of genes that can be amplified or deleted in genetic disorders or cancers. In many cases, tumor classification can be aided by identifying characteristic patterns of gene amplification or deletion (Pollack et al. (1999) Nature Genetics 23: 41–46; Arribas et al. (1999) Clin. Cancer Res. 5: 3454–9; Tanner et al. (1995) Clin. Cancer Res. 1: 1455–61). Methods of mutation analysis that rely on PCR are difficult to quantitate, and those that rely on gel electrophoresis are time-consuming and can only analyze a limited number of genes in a single test. SNPs can also be detected by mass spectrometry-based methods that detect molecular weight differences of DNA fragments that contain SNP sites. This method is limited by the resolution of mass spectrometry and on the requirement for expensive equipment The present invention recognizes that it is difficult to obtain reliable quantitative data on the expression of genes using solid supports, and that it is difficult, labor-intensive, and time-consuming to obtain information on the expression of genes using current Rnase-protection methods. The present invention also recognizes that there is a need to efficiently characterize particular mutations or sequence variations, such as SNPs or gene amplifications, that may characterize certain disease states or genotypes and that can provide information on the sequence of genes that are expressed by a subject.

BRIEF DESCRIPTION OF THE FIGURES

FIG. 3 depicts one aspect of the present invention, in which two survey populations of RNA are separately hybridized to sets of labeled probe nucleic acid molecules, where the set of probe nucleic acid molecules hybridizing to the first survey population carries a different label than the set of probe nucleic acid molecules hybridizing to the second survey population, and the nucleolytic activity-protected probe molecules are hybridized to the same array.

SUMMARY

Figure 1A:
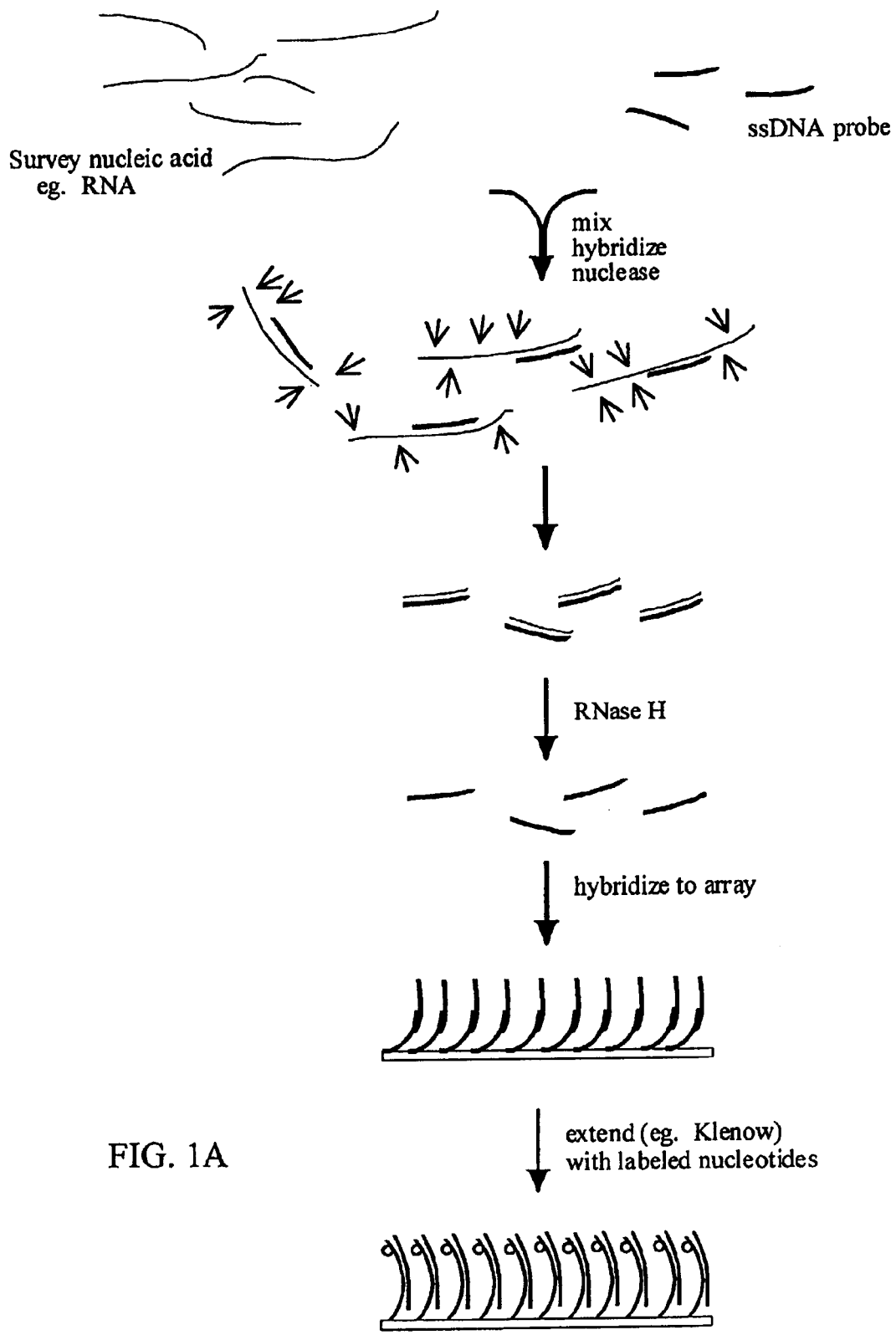
FIG. 1A depicts one aspect of the present invention in which expressed genes are identified from a population of RNA molecules using nucleic acid array hybridization of a nucleolytic activity-protected DNA probe, and incorporation of labeled nucleotides on an array.

The present invention recognizes that identifying genes expressed during developmental processes, stress responses, and disease states can advance understanding of these biological functions, and can contribute to identifying targets for therapeutic drugs. In addition, the present invention recognizes that rapid and reliable profiling of genetic variations, such as mutations and SNPs, is of increasing importance to diagnostics, prognostics, forensics, heredity determinations, and pharmacogenetics.

One aspect of the present invention provides a method of identifying one or more nucleic acid molecules that are expressed under a given set of conditions based on their complementarity to known sequences, or one or more mutations or SNPs in a population of nucleic acid molecules. The method includes: contacting at least one probe nucleic acid molecule with a survey population of nucleic acid molecules under conditions that promote nucleic acid hybridization to generate a probe-survey population mixture of nucleic acid molecules, treating the probe-survey population mixture of nucleic acid molecules with a nucleolytic activity, such that nucleolytic activity-sensitive nucleic acid molecules are digested, and contacting the resulting mixture of nucleolytic activity-protected nucleic acid molecules with a solid support comprising one or more attached nucleic acid molecules to generate attached nucleic acid molecule/nucleolytic activity-protected nucleic acid molecule complexes, and identifying one or more of the attached nucleic acid molecules or one or more of the nucleolytic activity-protected nucleic acid molecules in one or more attached nucleic acid molecule/nucleolytic activity-protected nucleic acid molecule complexes.

Another aspect of the present invention provides compositions that can be used for carrying out the methods of the present invention. Such compositions can be in the form of kits, and comprise a solid support comprising a first population of attached nucleic acids, and a second population of nucleic acids not attached to the solid support. Members of the second population of nucleic acid molecules can be at least partially complementary to members of the first population of attached nucleic acid molecules or can be at least partially identical to members of the first population of attached nucleic acid molecules, and can comprise at least one detectable label. Such kits can also include other components, such as at least one additional population of nucleic acid molecules, such as one or more nucleolytic activities, such as one or more polymerases, such as buffers and reagents, and/or such as one or more preparations of nucleotides, one or more of which may comprise a detectable label.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures in cell culture, chemistry, microbiology, molecular biology, cell science and cell culture described below are well known and commonly employed in the art. Conventional methods are used for these procedures, such as those provided in the art and various general references (Sambrook et al., *Molecular Cloning: A Laboratory Manual*, 2nd edition, Cold Spring Harbor Press, Cold Spring Harbor, N.Y. (1989); Ausubel et al., *Current Protocols in Molecular Biology*, John Wiley and Sons (1998); Harlowe and Lane, *Antibodies, a Laboratory Manual*, Cold Spring Harbor Press (1988)). Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

"Organism" can be any prokaryote or eukaryote, and includes viruses, protozoans, and metazoans. Metazoans include vertebrates and invertebrates. "Organism" can also ref to more than one species that are found in association with one another, such as mycoplasm-infected cells, a plasmodium-infected animal, etc.

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases such as 2-aminoadenine and the like. A nucleic acid molecule of the present invention can have linkages other than phosphodiester linkages. A nucleic acid molecule can also be a peptide nucleic acid molecule. A nucleic acid molecule can be of any length, and can be single-stranded or double-stranded, or partially single-stranded and partially double-stranded.

A "probe" or "probe nucleic acid molecule" is a nucleic acid molecule that is at least partially single-stranded, and that is at least partially complementary, or at least partially substantially complementary, to a sequence of interest. A probe can be RNA, DNA, or a combination of both RNA and DNA. It is also within the scope of the present invention to have probe nucleic acid molecules comprising nucleic acids in which the backbone sugar is other that ribose or deoxyribose. Probe nucleic acids can also be peptide nucleic acids. A probe can comprise nucleolytic-activity resistant linkages or detectable labels, and can be operably linked to other moieties, for example a peptide.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U). For example, the nucleotide sequence 5'-TATAC-3' is complementary to the nucleotide sequence 5'-GTATA-3'.

"Substantially complementary" refers to nucleic acids that will selectively hybridize to one another under stringent conditions.

"Selectively hybridize" refers to detectable specific binding. Polynucleotides, oligonucleotides and fragments thereof selectively hybridize to target nucleic acid strands, under hybridization and wash conditions that minimize appreciable amounts of detectable binding to nonspecific nucleic acids. High stringency conditions can be used to achieve selective hybridization conditions as known in the art Generally, the nucleic acid sequence complementarity between the polynucleotides, oligonucleotides, and fragments thereof and a nucleic acid sequence of interest will be at least 30%, and more typically and preferably of at least 40%, 50%, 60%, 70%, 80%, 90%, and can be 100%. Conditions for hybridization such salt concentration, temperature, detergents, and denaturing agents such as formamide can be varied to increase the stringency of hybridization, that is, the requirement for exact matches of C to base pair with G, and A to base pair with T or U, along the strand of nucleic acid.

"Corresponds to" refers to a polynucleotide sequence that shares identity (for example is identical) to all or a portion of a reference polynucleotide sequence. In contradistinction, the term "complementary to" is used herein to mean that the complementary sequence will base pair with all or a portion of a reference polynucleotide sequence. For illustration, the nucleotide sequence 5'-TATAC-3' corresponds to a reference sequence 5'-TATAC-3' and is complementary to a reference sequence 5'-GTATA-3'.

"Sequence identity" or "identical" means that two polynucleotide sequences are identical (for example, on a nucleotide-by-nucleotide basis) over the window of comparison. "Partial sequence identity" or "partial identity" means that a portion of the sequence of a nucleic acid molecule is identical to at least a portion of the sequence of another nucleic acid molecule.

"Substantial identity" or "substantially identical" as used herein denotes a characteristic of a polynucleotide sequence, wherein the polynucleotide comprises a sequence that has at least 30 percent sequence identity, preferably at least 50 to 60 percent sequence identity, more usually at least 60 percent sequence identity as compared to a reference sequence over a comparison window of at least 20 nucleotide positions, frequently over a window of at least 25 to 50 nucleotides, wherein the percentage of sequence identity is calculated by comparing the reference sequence to the polynucleotide sequence that may include deletions or addition which total 20 percent or less of the reference sequence over the window of comparison. "Substantial partial sequence identity" or "substantially partially identical" is used when a portion of a nucleic acid molecule is substantially identical to at least a portion of another nucleic acid molecule. As used herein "identity" or "identical" refers to the base composition of nucleic acids, and not to the composition of other components, such as the backbone that can be comprised of one or more sugars and one or more phosphates, or can have other substituted moieties.

A "detectable label" is a compound or molecule that can be detected, or that can generate a readout, such as fluorescence, radioactivity, color, chemiluminescence or other readouts known in the art or later developed. The readouts can be based on fluorescence, such as by fluorescent labels, such as but not limited to, Cy-3, Cy-5, phycoerynin, phycocyanin, allophycocyanin, FITC, rhodamine, or lanthanides; by flourescent proteins such as green fluorescent protein (GFP) and its variants, can be based on enzymatic activity, such as, but not limited to, the activity of beta-galactosidase, beta-lactamase, horseradish peroxidase, alkaline phosphatase, or luciferase; or can be based on radioisotopes (such as $^{33}P$, $^{3}H$, $^{14}C$, $^{35}S$, $^{125}I$, $^{32}P$ or $^{131}I$). A label optionally can be a base with modified mass, such as, for example, pyrimidines modified at the C5 position or purines modified at the N7 position. Mass modifying groups can be, for examples, halogen, ether or polyether, alkyl, ester or polyester, or of the general type XR, wherein X is a linking group and R is a mass-modifying group. One of skill in the art will recognize that there are numerous possibilities for mass-modifications useful in modifying nucleic acid molecules and oligonucleotides, including those described in Oligonucleotides and Analogues: A Practical Approach, Eckstein, ed. (1991) and in PCT/US94/00193.

"Label" or "labeled" refers to incorporation of a detectable marker, for example by incorporation of a fluorescent or radiolabled compound or attachment of moieties such as biotin that can be detected by the binding of a second moiety, such as marked avidin. Various methods of labeling nucleic acids are known in the art.

A "mutation" is a change in the genome with respect to the standard wild-type sequence. Mutations can be deletions, insertions, or rearrangements of nucleic acid sequences at a position in the genome, or they can be single base changes at a position in the genome, referred to as "point mutations". Mutations can be inherited, or they can occur in one or more cells during the lifespan of an individual.

"Operably linked" refers to a juxtaposition wherein the components so described are in a relationship permitting them to function in their intended manner. For example, a control sequence operably linked to a coding sequence is positioned in such a way that expression of the coding sequence is achieved under conditions compatible with control sequences.

A "sequence of interest" is a sequence whose presence or variation can be detected in one or more survey populations of nucleic acids by the methods of the present invention.

A "survey population of nucleic acid molecules" is a population of at least two nucleic acid molecules that are to be tested for the presence of a sequence of interest. A survey population of nucleic acid molecules can be DNA or RNA. A survey population of nucleic acid molecules can be from any source, such as a human source, animal source, plant source, or microbial source. The survey population can be isolated from tissue (including but not limited to hair, blood, serum, amniotic fluid, semen, urine, saliva, throat or genital swabs, biopsy samples, or autopsy samples) or cells, including cells grown in culture, and can be isolated from living or nonliving samples or subjects. The survey population can be isolated from inanimate material, remnants or artifacts, including fossilized material.

"Hybridization" is the process of base-pairing of single-stranded nucleic acids, or single-stranded portions of nucleic acids, to create double-stranded nucleic acids or double-stranded portions of nucleic acid molecules.

"Probe survey population mixture of nucleic acid molecules" refers to a mixture that contains probe nucleic acid molecules and survey population nucleic acid molecules. Preferably, the probe nucleic acid molecules and survey population molecules have been contacted under conditions that promote hybridization between nucleic acid molecules that are at least partially complementary or at least partially substantially complementary.

A "nucleolytic activity" or "nucleolytic agent" is an activity that can cleave nucleosidic bonds to degrade nucleic acid molecules. Nucleolytic activities or agents can be enzymes, such as, for example, Dnase I, Exonuclease III, Mung Bean Nuclease, S1 Nuclease, RNAse H, or Rnase A, or can be chemical compounds, such as hydrogen peroxide, osmium tetroxide, hydroxylamine, or potassium permanganate, or can be chemical conditions, such as high or low pH.

An "overhang" is a single-stranded region at a terminus of an otherwise double-stranded nucleic acid molecule.

An "attached nucleic acid molecule" is a nucleic acid molecule that is bound to a solid support. An attached nucleic acid molecule can be of any length, can be single-stranded or double-stranded, or partially single-stranded and partially double-stranded, and can comprise non-naturally occurring linkages, such as nucleolytic activity-resistant backbone linkages, such as but not limited to phosporothioate, methyl phosphonate, or borano-phosphate linkages. An attached nucleic acid molecule can be DNA, RNA, or a combination of DNA and RNA. It is also within the scope of the present invention to have probe nucleic acid molecules comprising nucleic acids in which the backbone sugar is other than ribose or deoxyribose; for example, certain hexoses may be substituted. Probe nucleic acids can also be peptide nucleic acids. The attached nucleic acid molecule can be reversibly or irreversibly bound to the solid support. The binding to the solid support can be direct or indirect. If the attached nucleic acid is directly bound, it can be attached to the solid support at its 3' or 5' terminus.

An "attached nucleic acid molecule/nucleolytic activity-protected nucleic acid molecule complex" or "hybridized complex" is a complex that includes at least one attached nucleic acid molecule and includes at least one nucleic acid molecule that has been treated with a nucleolytic activity. The nucleolytic activity-treated molecule of the hybridized complex can be a nucleic acid molecule that was portion of a nucleic acid molecule that was partially digested by a nucleolytic activity or can be a nucleic acid molecule that was wholly protected from nucleolytic activity. The attached nucleic acid molecule and the nucleolytic activity-protected nucleic acid molecule of the hybridized complex are preferably at least partially complementary. The hybridized complex can comprise other components as well, such as, but not limited to, additional nucleic acid molecules. One or more nucleic acid molecules of the hybridized complex can comprise a detectable label.

A "nucleolytic activity-protected nucleic acid molecule" is at least one nucleic acid molecule that has been treated with one or more nucleolytic activities, and that has not been degraded by the nucleolytic activities. A nucleolytic activity protected nucleic acid molecule can be single-stranded or may be double-stranded, or may be partially single-stranded and partially double-stranded. A nucleolytic activity-protected nucleic acid molecule can be resistant to one or more nucleolytic activities. Resistance to nucleolytic activities can be conferred, for example, by conformation of a nucleic acid molecule when it was treated with a nucleolytic activity (including being in the double-stranded state), by the nucleotide sequence of a nucleic acid molecule, or by one or more nucleoside linkages of a nucleic acid molecule. A nucleolytic activity-protected nucleic acid molecule can be a nucleolytic activity-protected survey population nucleic acid molecule or fragment thereof, or a nucleolytic activity-protected probe nucleic acid molecule or fragment thereof, or can comprise all or portions of both survey population nucleic acid molecules and probe nucleic acid molecules. In addition, in some embodiments, attached nucleic acid molecules or portions thereof can be nucleolytic activity-protected nucleic acid molecules. Nucleolytic activity-protected nucleic acid molecules can include or be operably linked to other compounds as well, for example, peptides, chemical moieties, and/or labels.

A "nucleolytic activity-protected nucleic acid molecule complex" or "protected complex" is a complex that includes one or more nucleic acid molecules that have been treated with one or more nucleolytic activities. One or more of the nucleic acid molecules of a protected complex, or one or more portions of a protected complex may be single-stranded. One or more of the nucleic acid molecules of a protected complex, or one or more portions of the nucleic acid molecules of a protected complex may be double-stranded. Typically, nucleic acid molecules of a nucleolytic activity-protected nucleic acid complex are resistant to one or more nucleolytic activities, such that they have not been degraded by one or more nucleolytic activities. Resistance to nucleolytic activities can be conferred, for example, by conformation of nucleic acid molecules (including being in the double-stranded state), by the nucleotide sequence of nucleic acid molecules, or by one or more nucleoside linkages of nucleic acid molecules. A nucleolytic activity-protected nucleic acid complex can include other compounds as well, for example, peptides, chemical moieties, and/or labels.

A "signal nucleic acid molecule" is a nucleic acid molecule that is at least partially single-stranded, and that is at least partially complementary, or at least partially substantially complementary, or at least partially identical, or at least partially substantially identical to a sequence of interest. A probe can be RNA, DNA, or a combination of both RNA and DNA. It is also within the scope of the present invention to have probe nucleic acid molecules comprising nucleic acids in which the backbone sugar is other than ribose or deoxyribose; for example, certain hexoses may be substituted. Probe nucleic acids can also be peptide nucleic acids. A probe can comprise nuclease resistant linkages and can be operably linked to other moieties, for example a peptide or a chemical moiety such as biotin. A signal nucleic acid molecule preferably comprises a detectable label.

A "single nucleotide polymorphism" or "SNP" is a position in a nucleic acid sequence that differs in base composition in nucleic acids isolated from different individuals of the same species.

A "solid support" is a solid material having a surface for attachment of molecules, compounds, cells, or other entities. The surface of a solid support can be flat or not flat. A solid support can be porous or non-porous. A solid support can be a chip or array that comprises a surface, and that may comprise glass, silicon, nylon, polymers, plastics, ceramics, or metals. A solid support can also be a membrane, such as a nylon, nitrocellulose, or polymeric membrane, or a plate or dish and can be comprised of glass, ceramics, metals, or plastics, such as, for example, a 96-well plate made of, for example, polystyrene, polypropylene, polycarbonate, or polyallomer. A solid support can also be a bead or particle of any shape, and is preferably spherical or nearly spherical, and preferably a bead or particle has a diameter or maximum width of 1 millimeter or less, more preferably of between 0.5 to 100 microns. Such particles or beads can be comprised of any suitable material, such as glass or ceramics, and/or one or more polymers, such as, for example, nylon, polytetrafluoroethylene, TEFLON™, polystyrene, polyacrylamide, sepaharose, agarose, cellulose, cellulose derivatives, or dextran, and/or can comprise metals, particularly paramagnetic metals, such as iron.

"Specific binding member" is one of two different molecules having an area on the surface or in a cavity which specifically binds to and is thereby defined as complementary with a particular spatial and polar organization of the other molecule. A specific binding member can be a member of an immunological pair such as antigen-antibody, biotin-avidin, hormone-hormone receptor, nucleic acid duplexes, IgG-protein A, DNA-DNA, DNA-RNA, and the like.

"Substantially linear" means that, when graphed, the increase in the product with respect to time conforms to a linear progression, or conforms more nearly to an arithmetic progression than to a geometric progression.

Introduction

The present invention recognizes that currently available technologies for the quantitative analysis of expressed genes are labor-intensive, time-consuming, and difficult to apply. There is a need to provide methods and compositions for obtaining gene expression profiles that can provide rapid, reliable, quantitative information on the expression of many genes in a single analysis. The present invention also recognizes that current methods for the analysis of gene mutations and SNPs use DNA that is amplified by methods such as PCR. Such amplification can introduce errors into the sequences being studied. Moreover, such methods do not distinguish between genes that are expressed and genes that are not expressed in a cell or organism of interest.

The present invention provides improved methods for gene expression analysis and gene mutation and SNP detection. The invention provides other benefits as well.

As a non-limiting introduction to the breadth of the present invention, the present invention includes several general and useful aspects, including:

1) a method for identifying nucleic acid molecules that are expressed in one or more cells, tissues, or subjects;

2) a method for identifying one or more mutations or SNPs in a population of nucleic acids from one or more cells, tissues, samples, or subjects;

3) a composition including at least one solid support having at least one attached nucleic acid molecule, and a set of nucleic acids that are either at least partially complementary, or at least partially substantially complementary, or at least partially identical, or at least partially substantially identical, to at least one of the attached nucleic acid molecules.

These aspects of the invention, as well as others described herein, can be achieved using the methods, articles of manufacture, and compositions of the present invention. To gain a full appreciation of the scope of the present invention, it will be further recognized that various aspects of the present invention can be combined to make desirable embodiments of the invention.

I. Method of Identifying Expressed Nucleic Acid Molecules Using Nucleolytic Activities and Hybridization The present invention includes a method of identifying at least one expressed nucleic acid molecule, such as a nucleic acid molecule that is expressed in one or more cells. The present invention also includes a method of detecting nucleic acid molecules in a sample, such as a biological sample or environmental sample. The method includes: contacting at least one probe nucleic acid molecule with a survey population of nucleic acid molecules under conditions that promote hybridization between complementary nucleic acid molecules to generate a probe-survey population mixture of nucleic acid molecules, treating the probe-survey population mixture of nucleic acid molecules with a nucleolytic acitivity, such that nucleolytic activity-sensitive nucleic acid molecules are digested, to generate a population of nucleolytic activity-protected nucleic acid molecules; contacting said population of nucleolytic activity-protected nucleic acid molecules with a solid support comprising one or more attached nucleic acid molecules under conditions that promote hybridization between nucleic acid molecules to generate attached nucleic acid molecule/nucleolytic activity-protected nucleic acid molecule complexes; and identifying one or more of said attached nucleic acid molecules or one or more of said nucleolytic activity-protected nucleic acid molecules in one or more attached nucleic acid molecule/nucleolytic activity-protected nucleic acid molecule complexes.

The following description of preferred embodiments is provided for purposes of illustration, and not by way of limitation. It will be recognized that substitutions and combinations of methods, steps, and components described herein are within the scope of the present invention.

Embodiments Encompassing Expression Profiling

The present invention can be directed to expression profiling, in which the genes expressed by a particular organism, cell type, or tissue type can be identified. Expression profiling can be directed toward identifying genes expressed by one or more organisms at a particular time, at a particular stage of development, or under particular conditions. Expression profiling using the methods of the present invention can be performed quantitatively, such that relative amounts of gene expression can be determined.

It is recognized that the present invention can also be used to detect portions of genes, and thus the present invention can detect a region of a gene that is common to different gene transcripts and/or can detect more than one region of a single gene transcript. In these aspects probe nucleic acid molecules of the present invention can be designed such that they are at least partially complementary or at least partially substantially complementary to one or more than one region of a particular gene, and/or to one or more regions of a gene that may be shared among different gene transcripts, such as splice variants ("isoforms") of gene transcripts, gene transcripts originating from different members of a gene family, or variant gene transcripts produced by viruses.

The present invention can also be directed to detection of nucleic acids in a sample, such as, but not limited to, the detection of pathogen sequences in biological samples or contaminant sequences in environmental samples. The methods of the present invention can also be used to provide quantitative information of the copy number of a gene in one or more cells, such as a malignant cell. The following descriptions of embodiments depicted in the figures is by way of illustration and not by way of limitation.

A preferred embodiment of the present invention is depicted in FIG. 1A. In this example of expression profiling, the survey population is RNA, and a set of DNA probes is employed in which the probes are complementary to RNA transcripts known to be present or suspected of being present in the survey population. A set of attached nucleic acid molecules is also provided, in which the attached nucleic acid molecules are bound to a solid support in the form of an array, and in which the attached nucleic acid molecules are DNA oligonucleotides that are at least partially complementary to the probe nucleic acid molecules. In this embodiment, the set of probe nucleic acid molecules is contacted with the survey nucleic acid molecules under conditions that promote hybridization between complementary nucleic acids, and then the probe-survey population of nucleic acid molecules is contacted with a single-strand specific nuclease, such as Mung Bean nuclease, such that single-stranded nucleic acid molecules are digested. Following nuclease treatment, the nuclease is inactivated, for example by addition of EDTA. Protected probe-survey population of nucleic acid molecules are then treated, for example, with RNAse H, to remove the RNA strands hybridizing to the DNA probe, resulting in a solution of DNA probes that quantitatively represent the RNA transcripts to which they are complementary. In this embodiment, the single-stranded nucleic acids that are derived from the protected probe-survey population of nucleic acid molecules are probes that are complementary to expressed gene sequences. These protected nucleic acid molecules are hybridized to attached nucleic acid molecules on a DNA array. Attached and probe nucleic acid molecules are designed such that hybridization between complementary attached and probe nucleic acid molecules leaves single stranded overhangs on one or both ends of the hybridized complex. The number of single-stranded bases in a hybridized complex is standardized among all the possible complexes on the array. After washing to remove unhybridized nucleic acid molecules, the array is treated with a DNA polymerase, such as the Klenow fragment of *E. coli* DNA polymerase, and labeled nucleotides. The DNA polymerase extends an attached nucleic acid molecule using a protected nucleic acid molecule (in this embodiment, the protected probe nucleic acid molecules) as a template by incorporating labeled nucleotides. In this embodiment, the probe nucleic acid molecule cannot be extended by the DNA polymerase. This can be accomplished, for example, by making the 3' terminal nucleotide of the probe nucleic acid a dideoxynucleotide that does not permit extension. After washing the array, the array is scanned. Incorporation of label at a position on the array is indicative of the presence of a transcript in the survey population. The intensity of the signal at a position on the array is proportional to the number of hybridization complexes at that position, which directly reflects the number of transcripts of the gene that the attached nucleic acid molecule at that position corresponds to that are present in the survey population.

Figure 1B:
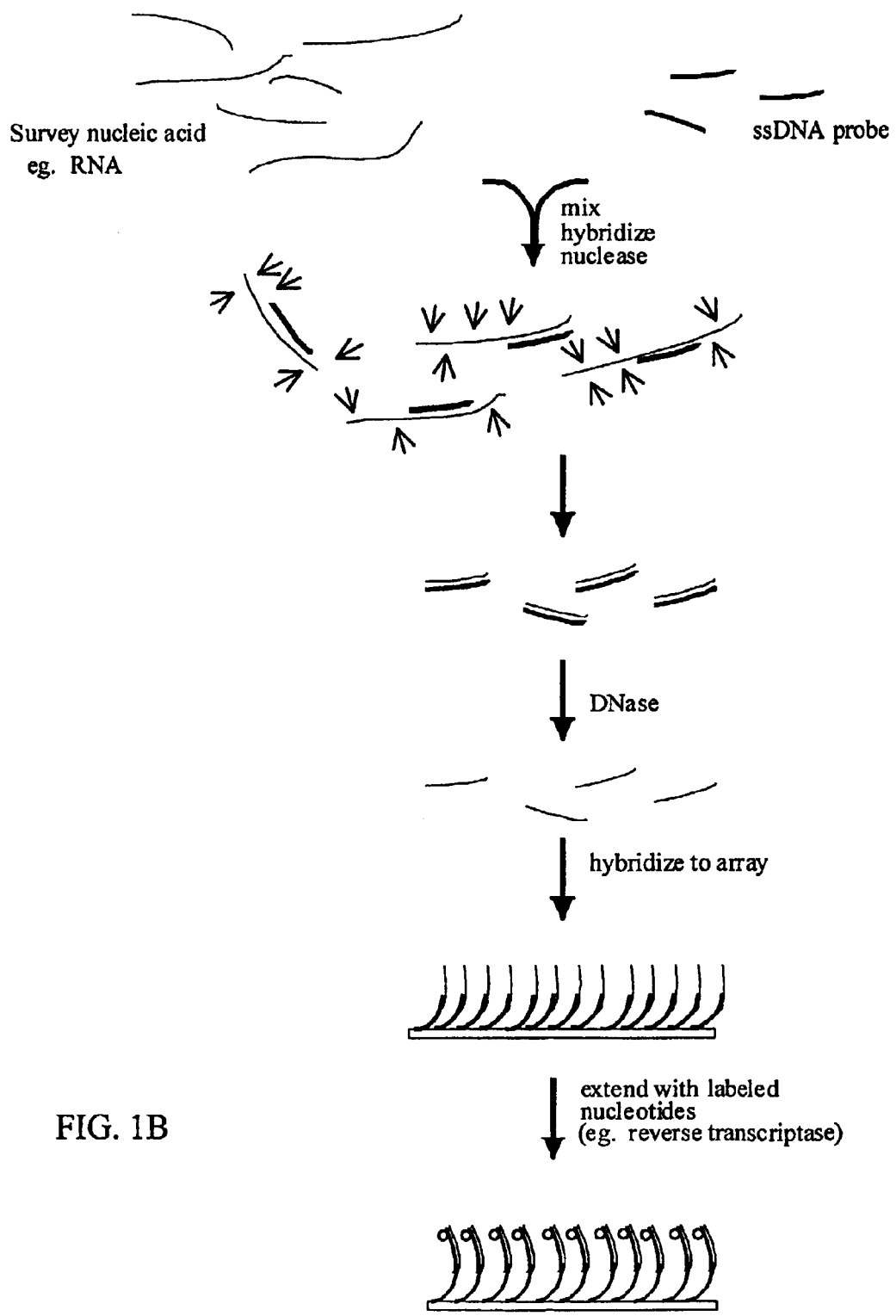
FIG. 1B depicts one aspect of the present invention in which expressed genes are identified from a population of RNA molecules using array hybridization of a nucleolytic activity-protected RNA fragment, and incorporation of labeled nucleotides on an array.

A variation on this embodiment is depicted in FIG. 1B, in which the survey population is RNA, and a set of DNA probes is employed in which the probes are complementary to RNA transcripts known to be present or suspected of being present in the survey population. A set of attached nucleic acid molecules is also provided, in which the attached nucleic acid molecules are bound to a solid support in the form of an array, and in which the attached nucleic acid molecules are DNA oligonucleotides that are at least partially identical to the probe nucleic acid molecules. In this embodiment, the set of probe nucleic acid molecules is contacted with the survey nucleic acid molecules under conditions that promote hybridization between complementary nucleic acids, and then the probe-survey population of nucleic acid molecules is treated, for example with Mung Bean nuclease, such that single-stranded nucleic acid molecules are digested. Following nuclease treatment, the nuclease is inactivated, for example by addition of EDTA. Protected probe-survey population of nucleic acid molecules are then treated with RNAse-free DNAse to remove the DNA probe nucleic acids hybridizing to the RNA survey population, resulting in a solution of protected RNA survey population fragments. These single-stranded nucleic acids that are derived from the protected probe-survey population of nucleic acid molecules are hybridized to attached nucleic acid molecules on a DNA array. As in the previous example, the number of unpaired bases in the hybridized complexes on the array can be controlled by appropriately standardizing the sizes of the probe and attached nucleic acid molecules. After washing to remove unhybridized nucleic acid molecules, the array is treated with a RNA-dependent DNA polymerase, such as MMLV reverse transcriptase, and labeled nucleotides. The reverse transcriptase extends the attached nucleic acid molecule using the protected nucleic acid molecule (in this instance, the survey population RNA fragments) as templates by incorporating labeled nucleotides. After washing the array, the array is scanned. Incorporation of label at a position on the array is indicative of the presence of a transcript in the survey population. The intensity of the signal at a position on the array is proportional to the number of hybridization complexes at that position, which directly reflects the number of transcripts of the gene to which the attached nucleic acid molecule at that position corresponds that are present in the survey population.

Figure 2:
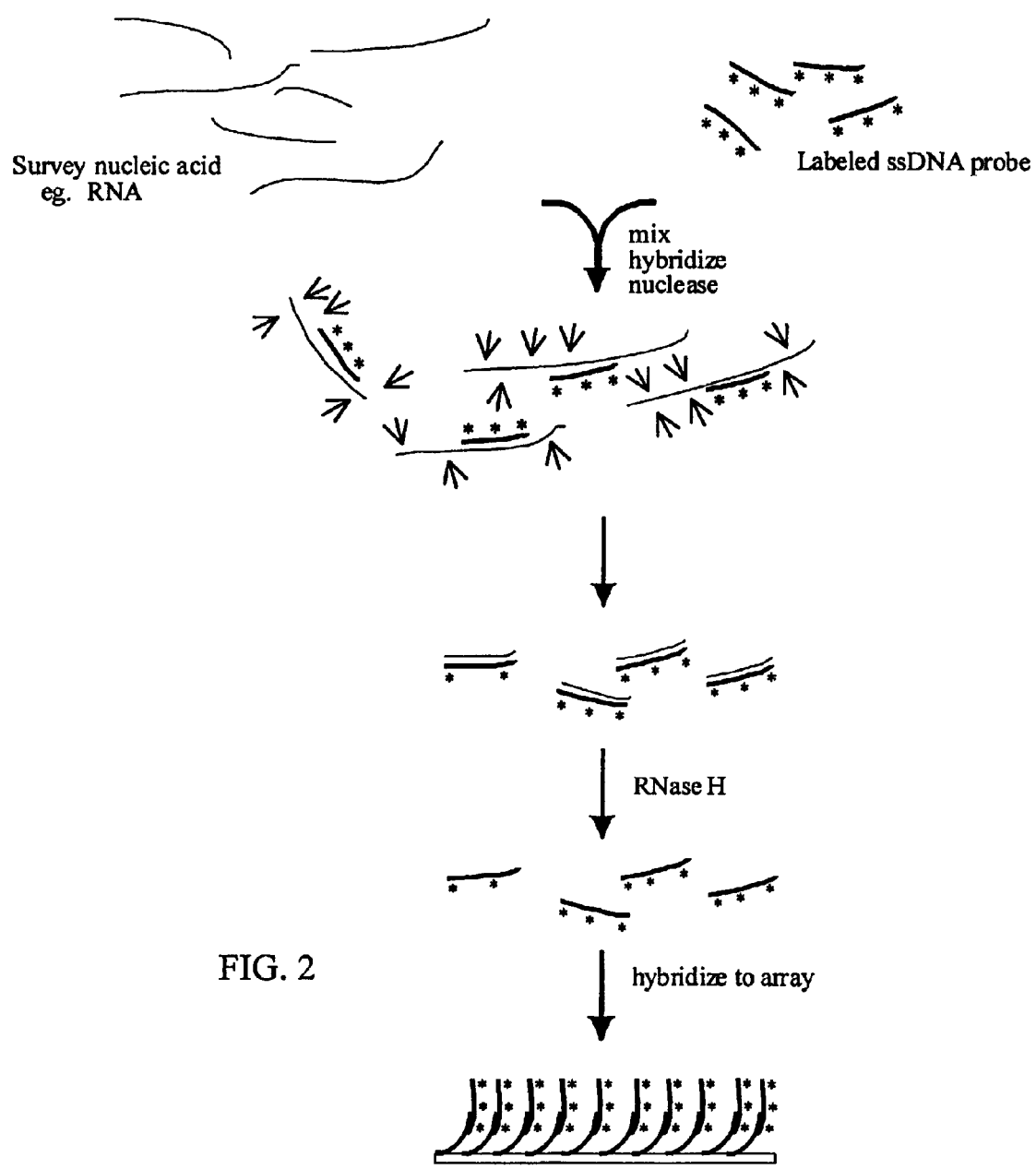
FIG. 2 depicts one aspect of the present invention, in which expressed genes are identified from a population of RNA molecules using array hybridization of a labeled nucleolytic activity-protected DNA probe.

In the embodiment depicted in FIG. 2, the survey population is RNA, and a set of DNA probes is employed in which the probes are complementary to RNA transcripts known to be present or suspected of being present in the survey population. The DNA probe nucleic acid molecules comprise at least one detectable label, such that members of the set of DNA probes preferably are labeled to the same specific activity, or will give rise to signals of the same or comparable intensity. A set of attached nucleic acid molecules is also provided, in which the attached nucleic acid molecules are bound to a solid support in the form of an array, and in which the attached nucleic acid molecules are DNA oligonucleotides that are at least partially complementary to the probe nucleic acid molecules. In this embodiment, the set of probe nucleic acid molecules is contacted with the survey nucleic acid molecules under conditions that promote hybridization between complementary nucleic acids, and then the probe-survey population of nucleic acid molecules is contacted with a single-strand specific nuclease, such that single-stranded nucleic acid molecules are digested. Following nuclease treatment, the nuclease is inactivated. Protected probe-survey population of nucleic acid molecules are then treated with an RNase to remove the RNA strands hybridizing to the DNA probe, resulting in a solution of single-stranded nucleic acids that are derived from the protected probe-survey population of nucleic acid molecules that are in fact a subset of the population of DNA probes. Members of this subset of DNA probes quantitatively and qualitatively represent the RNA transcripts to which they are complementary. The protected probe nucleic acid molecules are hybridized to attached nucleic acid molecules on a DNA array. After washing to remove unhybridized nucleic acid molecules, the array is scanned. Detection of label at a position on the array is indicative of the presence of a transcript in the survey population. The intensity of the signal at a position on the array is proportional to the number of hybridization complexes at that position, which directly reflects the number of transcripts of the gene to which the attached nucleic acid molecule at that position corresponds that are present in the survey population.

A variation of this method is depicted in FIG. 3, in which RNA transcript levels from two survey populations are detected on the same array. In this embodiment, the survey populations are RNA, for example, a first survey population of RNA extracted from normal cells and a second survey population of RNA extracted from abnormal cells. These survey populations are hybridized in separate reactions to DNA probe nucleic acid molecules. The set of probe nucleic acid molecules hybridized to the first survey population is identical in sequence composition to the set of probe nucleic acid molecules hybridized to the second survey population, but each set of probe nucleic acid molecules includes a different detectable label, such that the detectable label of the probe hybridizing to the first survey population is distinguishable from the detectable label of the probe hybridizing to the second survey population. After nuclease treatment of both probe-survey population nucleic acid mixtures, the protected complexes are RNase treated, and the protected probe nucleic acid molecules from both nuclease treatments are hybridized to the same array. After washing to remove unhybridized nucleic acid molecules, the array is scanned. Detection of label corresponding to the set of probes hybridized to the first survey population at a position on the array is indicative of the presence of a transcript in the first survey population, and detection of label corresponding to the set of probes hybridized to the second survey population at a position on the array is indicative of the presence of a transcript in the second survey population. Each position on the array can be identified as having no or negligible signal, or signal derived from one or both labels. The intensity of the different signals at a position on the array directly reflects the number of transcripts of the gene to which the attached nucleic acid molecule at that position corresponds that are present in each survey population, making it possible to determine the relative amount of expression of a gene of interest in two populations of RNA, where the RNA populations can be obtained from two different cell types, the same cell type under two different conditions, the same cell type in two different organisms, etc.

Figure 4:
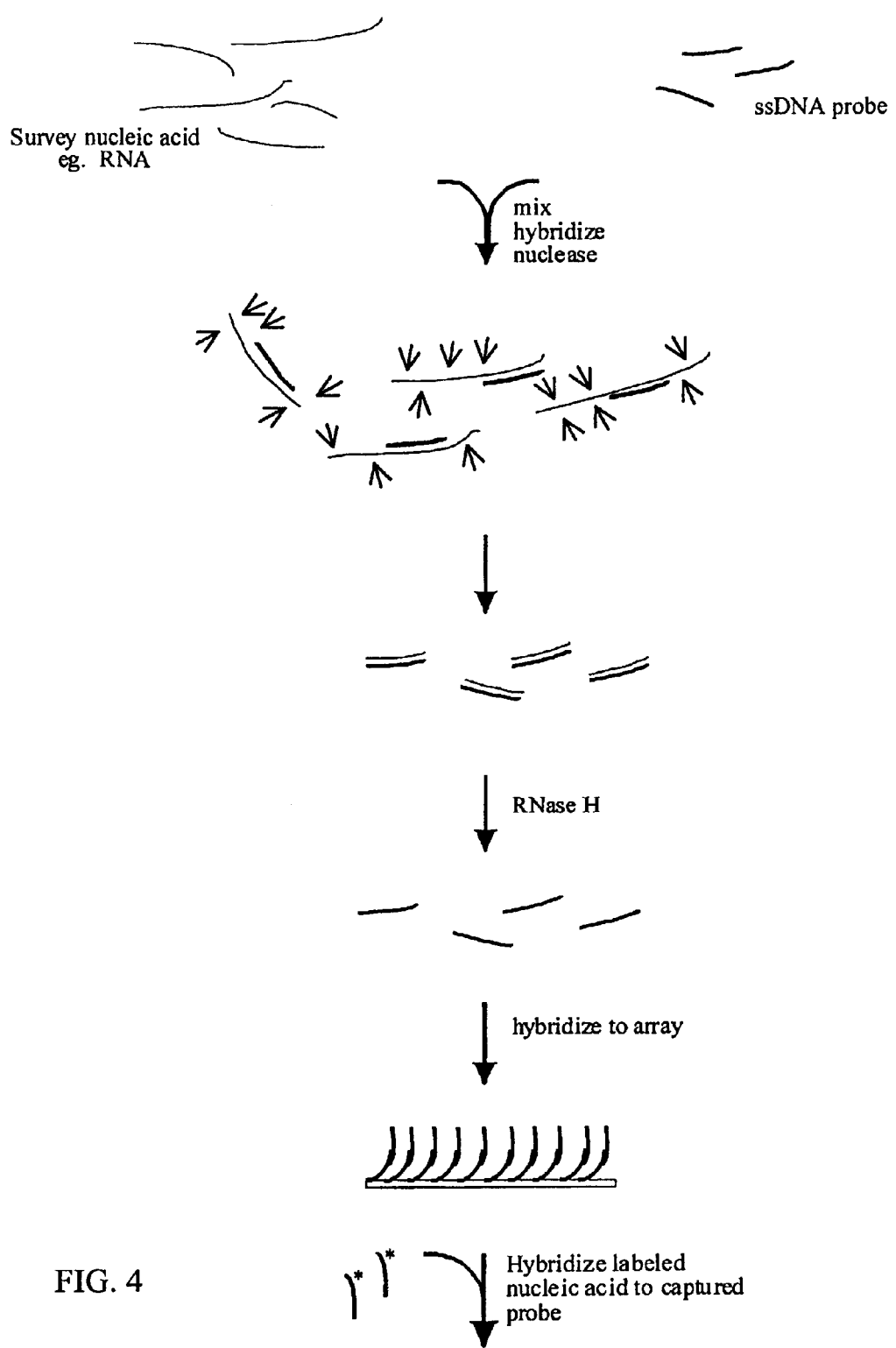
FIG. 4 depicts one aspect of the present invention, in which expressed genes are identified from a population of RNA molecules using array hybridization of a nucleolytic activity-protected DNA probe, and a labeled signal nucleic acid molecule is hybridized to the attached nucleic acid molecule/nucleolytic activity-protected nucleic acid molecule complexes on the array.

In yet another variation of expression profiling, depicted in FIG. 4, the survey population is RNA, and a set of DNA probes is employed in which the probes are complementary to RNA transcripts known to be present or suspected of being present in the survey population. A set of attached nucleic acid molecules is also provided, in which the attached nucleic acid molecules are bound to a solid support in the form of an array, and in which the attached nucleic acid molecules are DNA oligonucleotides that are at least partially complementary to the probe nucleic acid molecules. The probe nucleic acid molecules are partially complementary to the attached nucleic acid molecules, such that a portion of the probe nucleic acid molecule is complementary to the attached nucleic acid molecule, and a portion of the probe nucleic acid molecule is not complementary to the attached nucleic acid molecule. In this embodiment, the set of probe nucleic acid molecules is contacted with the survey nucleic acid molecules under conditions that promote hybridization between complementary nucleic acids, and then the probe-survey population of nucleic acid molecules is contacted with a single-strand specific nuclease, such that single-stranded nucleic acid molecules are digested. Following nuclease treatment, the nuclease is inactivated, for example by addition of EDTA. Protected probe-survey population of nucleic acid molecules are then treated, for example with RNAse H, to remove the RNA strands hybridizing to the DNA probe, resulting in a solution of single-stranded nucleic acids that are derived from the protected probe-survey population of nucleic acid molecules and are in fact a subset of the population of DNA probes. Members of this subset of DNA probes quantitatively and qualitatively represent the RNA transcripts to which they are complementary. The protected probe nucleic acid molecules are hybridized to attached nucleic acid molecules on a DNA array. After washing to remove unhybridized nucleic acid molecules, another set of signal nucleic acid molecules is hybridized to the array. The signal nucleic acid molecules are complementary to portions of the probe nucleic acid molecules that are not complementary to the attached nucleic acid molecules. The signal nucleic acid molecules are labeled with a detectable label, such that each signal nucleic acid molecule gives rise to a signal of the same or comparable intensity. After washing, the array is scanned. Detection of one or more labels at a position on the array is indicative of the presence of a transcript in the survey population. The intensity of the signal at a position on the array is proportional to the number of hybridization complexes at that position, which directly reflects the number of transcripts of the gene to which the attached nucleic acid molecule at that position corresponds that are present in the survey population.

Figure 5:
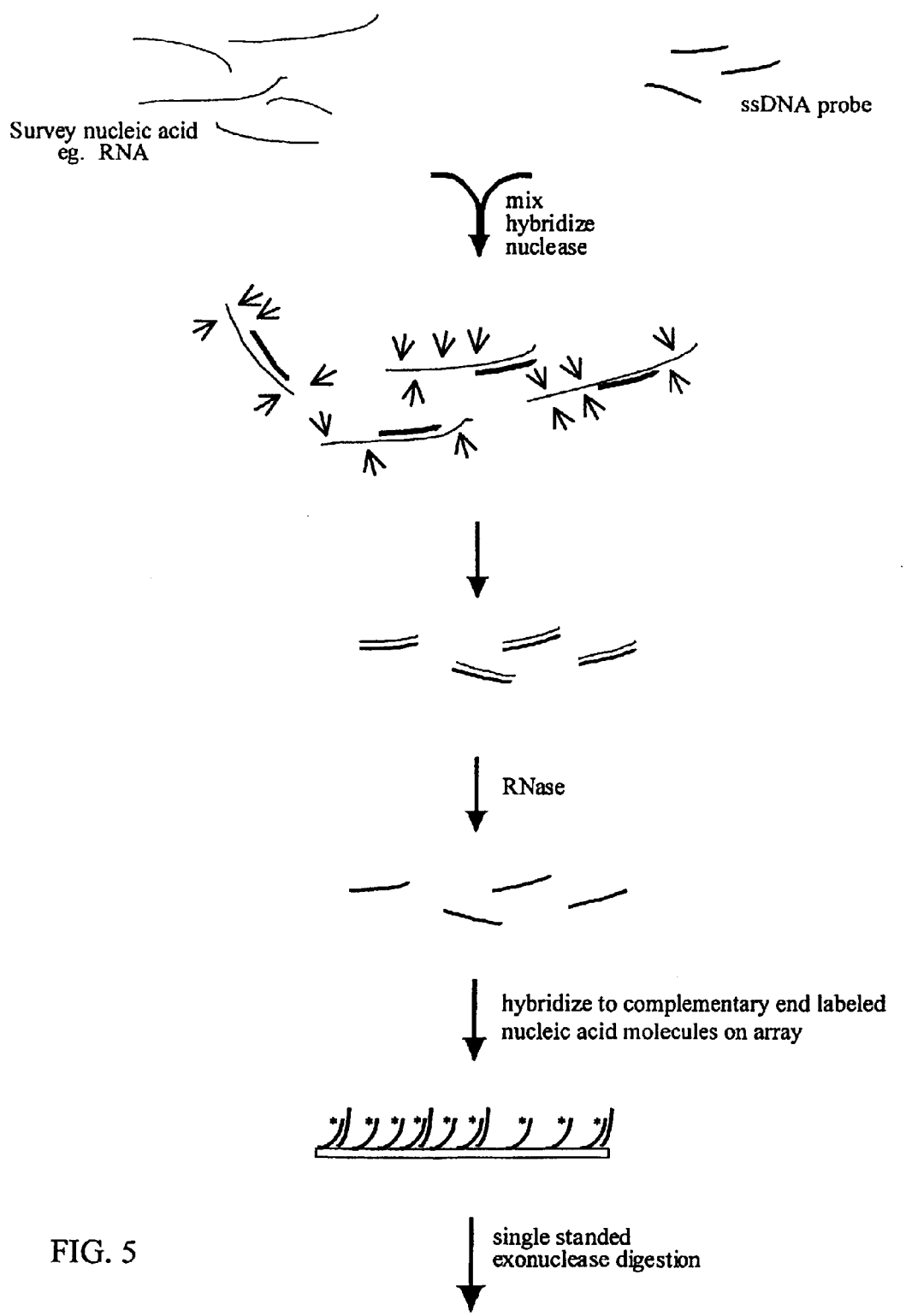
FIG. 5 depicts one aspect of the present invention, in which expressed genes are identified from a population of RNA molecules using array hybridization of a nucleolytic activity-protected DNA probe, the attached nucleic acid molecules are labeled, and the array is treated with a nucleolytic activity following hybridization.

FIG. 5 illustrates yet another embodiment of the present invention in which the survey population is RNA, and a set of DNA probes is employed in which the probes are complementary to RNA transcripts known to be present or suspected of being present in the survey population. A set of attached nucleic acid molecules is also provided, in which the attached nucleic acid molecules are bound to a solid support in the form of an array, and in which the attached nucleic acid molecules are DNA oligonucleotides that are at least partially complementary to the probe nucleic acid molecules. The attached nucleic acid molecules are detectably labeled, such that attached nucleic acids on the same array give rise to detectable signals of the same or comparable intensity. Preferably, the attached nucleic acid molecules have one or more nuclease-resistant linkages, such as phosphothioate linkages, in the portion of the attached nucleic acid molecule that is proximal to the array, and have one or more nuclease-sensitive linkages, such as phosphodiester linkages, in the portion of the attached nucleic acid molecule that is not proximal to the array. The detectable label is incorporated into or linked to the portion of the nucleic acid molecule that comprises nuclease-sensitive linkages. The probe nucleic acid molecules are partially complementary to the attached nucleic acid molecules, such that when a probe nucleic acid molecule is hybridized to an attached nucleic acid molecule, the regions of a hybridized attached nucleic acid molecules that are nuclease-sensitive and comprise the detectable label are base-paired with a probe nucleic acid molecule. In this embodiment, the set of probe nucleic acid molecules is contacted with the survey nucleic acid molecules under conditions that promote hybridization between complementary nucleic acids, and then the probe-survey population of nucleic acid molecules is contacted with a nucleolytic activity such as Mung Bean nuclease, such that single-stranded nucleic acid molecules are digested. Following nuclease treatment, the nuclease is inactivated, for example by addition of EDTA. Protected probe-survey population of nucleic acid molecules are then treated, for example with RNAse H, to remove the RNA strands hybridizing to the DNA probe, resulting in a solution of single-stranded nucleic acids that are derived from the protected probe-survey population of nucleic acid molecules and are in fact a subset of the population of DNA probes. Members of this subset of DNA probes quantitatively and qualitatively represent the RNA transcripts to which they are complementary. The protected probe nucleic acid molecules are hybridized to attached nucleic acid molecules on a DNA array. After washing to remove unhybridized nucleic acid molecules, another nuclease treatment with Mung Bean nuclease is performed on the chip, such that single-stranded nuclease-sensitive nucleic acid linkages are cleaved. Label that has been incorporated into the attached nucleic acid molecule is released from the array unless there is hybridization of the attached nucleic acid molecule to a probe nucleic acid molecule, rendering it resistant to nuclease digestion. After washing, the array is scanned. Detection of label at a position on the array is indicative of the presence of a transcript in the survey population. The intensity of the signal at a position on the array is proportional to the number of hybridization complexes at that position, which directly reflects the number of transcripts of the gene to which the attached nucleic acid molecule at that position corresponds that are present in the survey population.

Embodiments Encompassing Mutation and SNP Detection

The methods and compositions of the present invention can also be directed to the detection of mutations or SNPs. Mutation or SNP detection can be directed toward identifying mutations or SNPs in expressed genes by using RNA as the survey population, although that is not a requirement of the present invention.

Figure 6A:
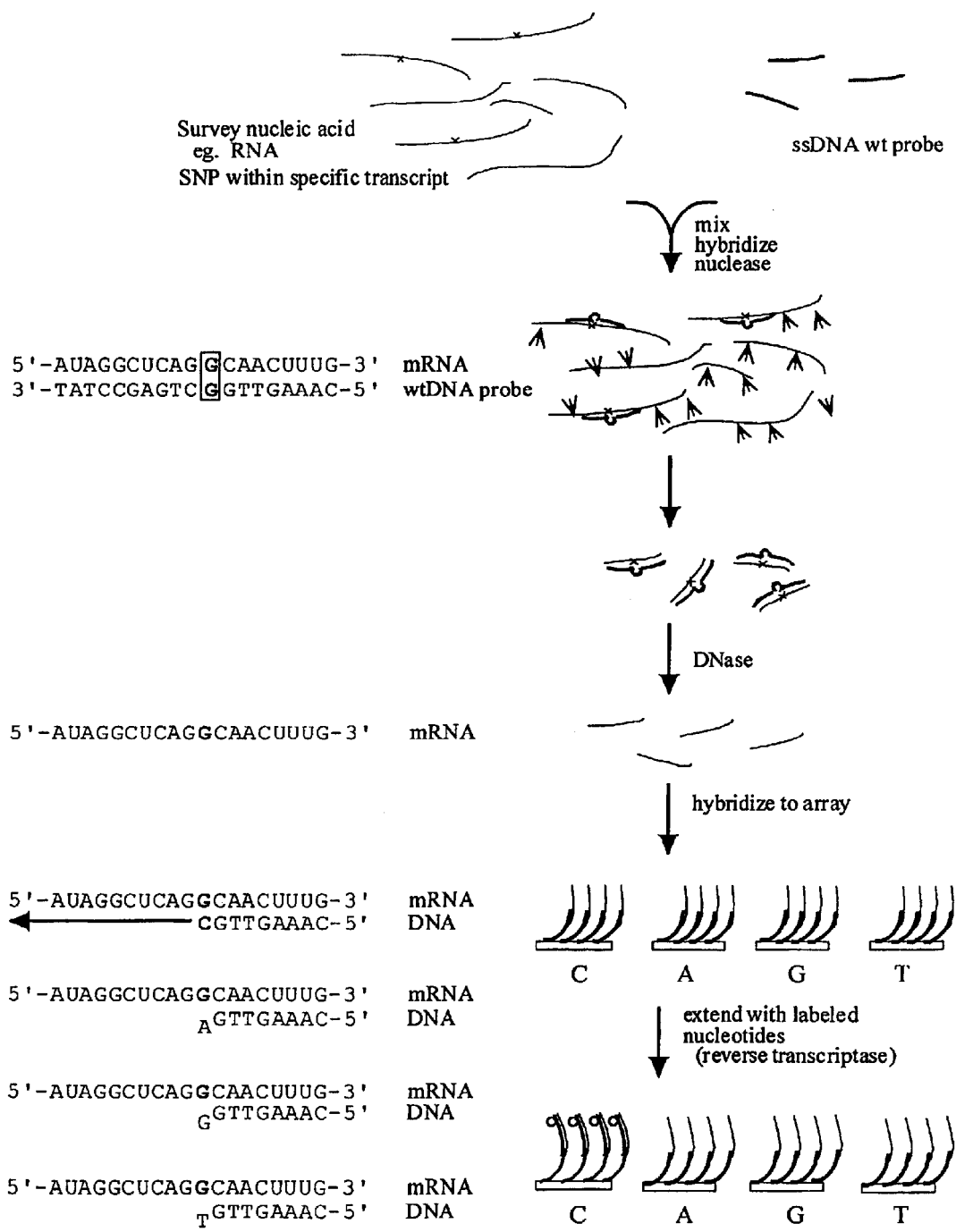
FIG. 6A depicts one aspect of the present invention, in which mutations or SNPs are detected from a population of RNA molecules by hybridization of nucleolytic activity-protected RNA fragments to an array, and incorporation of labeled nucleotides on an array.

In a preferred embodiment of the present invention, depicted in FIG. 6A, the survey population is RNA, and a set of DNA probes is employed in which the probes are complementary to RNA transcripts known to be present or suspected of being present in the survey population. A set of attached nucleic acid molecules is also provided, in which the attached nucleic acid molecules are bound to a solid support in the form of an array, and in which the attached nucleic acid molecules are DNA oligonucleotides that are partially complementary to the probe nucleic acid molecules. The 3' ends of the attached nucleic acid molecules are unattached, and the 3' termini of attached nucleic acid molecules are known or suspected SNP sites. In this embodiment, the probe nucleic acid molecules include DNA sequences that include a known or suspected SNP, where the known or suspected mutation or SNP is not at the terminus of the probe nucleic acid molecules. One region of the probe nucleic acid molecule is at least partially identical or at least partially substantially identical to the attached nucleic acid molecule, and another region of the probe nucleic acid molecule is not identical or substantially identical to the attached nucleic acid molecule. The probe nucleic acid molecules are contacted with the survey nucleic acid molecules under conditions that promote hybridization between complementary nucleic acids, and then the probe-survey population of nucleic acid molecules is contaced, for example with Mung Bean nuclease, a single-strand specific nuclease, such that single-stranded nucleic acid molecules are digested. Following nuclease treatment, the nuclease is inactivated, for example by addition of EDTA. The protected probe-survey population of nucleic acid molecules are then treated, for example with RNAse-free DNase to remove the DNA probe sequences hybridizing to the RNA, resulting in a solution of RNA fragments that encompass known or suspected mutation or SNP sites. These protected nucleic acid molecules are hybridized to attached nucleic acid molecules on a DNA array. Attached and probe nucleic acid molecules are designed such that hybridization between complementary attached and protected nucleic acid molecules leaves single stranded overhangs of protected RNA molecules on the hybridized complex. The single-stranded region of the overhanging RNA strand of the hybridized complex begins at the mutation or SNP site, that may or may not be complementary between the protected RNA fragment and the attached nucleic acid molecule, depending on the sequence of the RNA at the mutation or SNP site. The array is treated with a polymerase, such as the MMLV reverse transcriptase, and labeled nucleotides. The polymerase extends the attached nucleic acid molecule using the protected nucleic acid molecule (in this instance, the protected RNA survey population nucleic acid molecule) as a template only if there is complementarity between the protected RNA fragment and the attached nucleic acid molecule at the mutation or SNP site. After washing the array, the array is scanned. Incorporation of label at a position on the array is indicative of precise complementarity between the attached nucleic acid molecule and the protected RNA molecule at the SNP site, and thus identifies the sequence at an SNP site in an expressed gene.

Figure 6B:
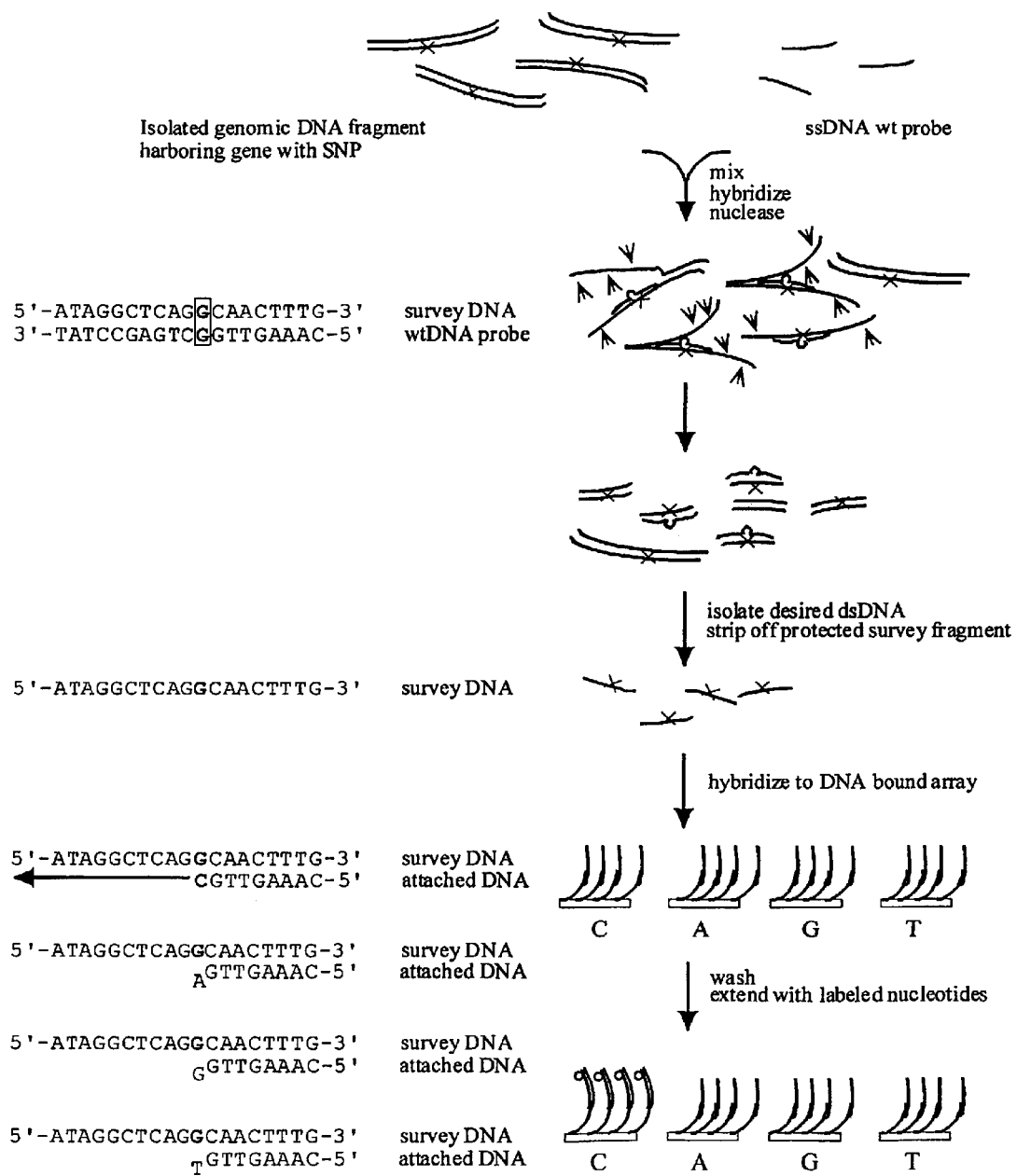
FIG. 6B depicts one aspect of the present invention, in which mutations or SNPs are detected from a survey population of DNA molecules by hybridization of nucleolytic-activity protected DNA fragments to an array, and incorporation of labeled nucleotides on an array.

In FIG. 6B, the method of SNP or mutation detection is not restricted to expressed genes. The survey population is DNA, and a set of DNA probes is employed in which the probes are complementary to DNA sequences known to be present or suspected of being present in the survey population In some aspects of this embodiment, the probe nucleic acid molecules can optionally be labeled with a specific binding member such as biotin, that can be used for capture of nucleolytic activity-protected probe-survey nucleic acid complexes. A set of attached nucleic acid molecules is also provided, in which the attached nucleic acid molecules are bound to a solid support in the form of an array, and in which the attached nucleic acid molecules are DNA oligonucleotides that are partially identical to the probe nucleic acid molecules. The 3' ends of the attached nucleic acid molecules are unattached, and the 3' termini of the attached nucleic acid molecules are known or suspected SNP sites. In this embodiment, the probe nucleic acid molecules include DNA sequences that include known or suspected mutation or SNP sites, where the known or suspected mutation or SNP site is not at the termini of the probe nucleic acid molecules. One region of the probe nucleic acid molecule is identical or substantially identical to the attached nucleic acid molecule, and another region of the probe nucleic acid molecule is not identical or substantially identical to the attached nucleic acid molecule. The probe nucleic acid molecules are contacted with the survey nucleic acid molecules under conditions that promote hybridization between complementary nucleic acids, and then the probe-survey population of nucleic acid molecules is contacted with a nucleolytic activity such as Mung Bean nuclease, a single-stand specific nuclease, such that single-stranded nucleic acid molecules are digested. Following nucleolytic activity treatment, the nucleolytic activity is inactivated, for example by addition of EDTA.

The protected probe-survey population of nucleic acid molecules can optionally be treated to render the protected survey population nucleic acid molecules single-stranded. The protected survey population nucleic acid molecules can also be substantially purified from the protected probe nucleic acid molecules. This can prevent the protected probe nucleic acid molecules from competing with attached nucleic acid molecules for hybridization to the protected survey population molecules during the hybridization step. In aspects where the probe comprises a biotin moiety, the nucleolytic activity-protected complexes can be collected by capture, for example with streptavidin-coated beads that bind the biotinylated probe nucleic acid molecules of the protected complexes. Protected survey nucleic acid molecule fragments can be stripped off the beads using conditions that denature double-stranded DNA (e.g., basic pH), leaving the probe nucleic acid molecules attached to the beads. The eluted protected survey nucleic acid molecules are collected and optionally concentrated, for example, by precipitation with ethanol for hybridization to attached nucleic acid molecules on a DNA array.

Attached and probe nucleic acid molecules are designed such that hybridization between complementary attached and protected nucleic acid molecules leaves single stranded overhangs of protected survey population nucleic acid molecules on the hybridized complex. The single-stranded region of the overhanging protected nucleic acid molecule strand of the hybridized complex begins at the mutation or SNP site, that may or may not be complementary between the protected nucleic acid molecule and the attached nucleic acid molecule, depending on the sequence of the survey population DNA at the mutation or SNP site. The array is treated with a DNA polymerase, such as the Klenow fragment, and labeled nucleotides. The polymerase extends the attached nucleic acid molecule using the protected nucleic acid molecule (in this embodiment, the protected survey population nucleic acid molecule) as a template only if there is complementarity between the protected survey population fragment and the attached nucleic acid molecule at the mutation or SNP site. Extension of the protected nucleic acid molecule using the attached nucleic acid molecule as a primer, which can lead to false positives, can be prevented by designing the entire attached nucleic acid molecule (with the exception of the SNP site) to be complementary to a portion of the protected survey population nucleic acid molecule. After washing the array, the array is scanned. Incorporation of label at a position on the array is indicative of precise complementarity between the attached nucleic acid molecule and the protected DNA molecule of the survey population at the SNP site, and thus identifies the sequence at a mutation or SNP site in a gene.

Figure 7A:
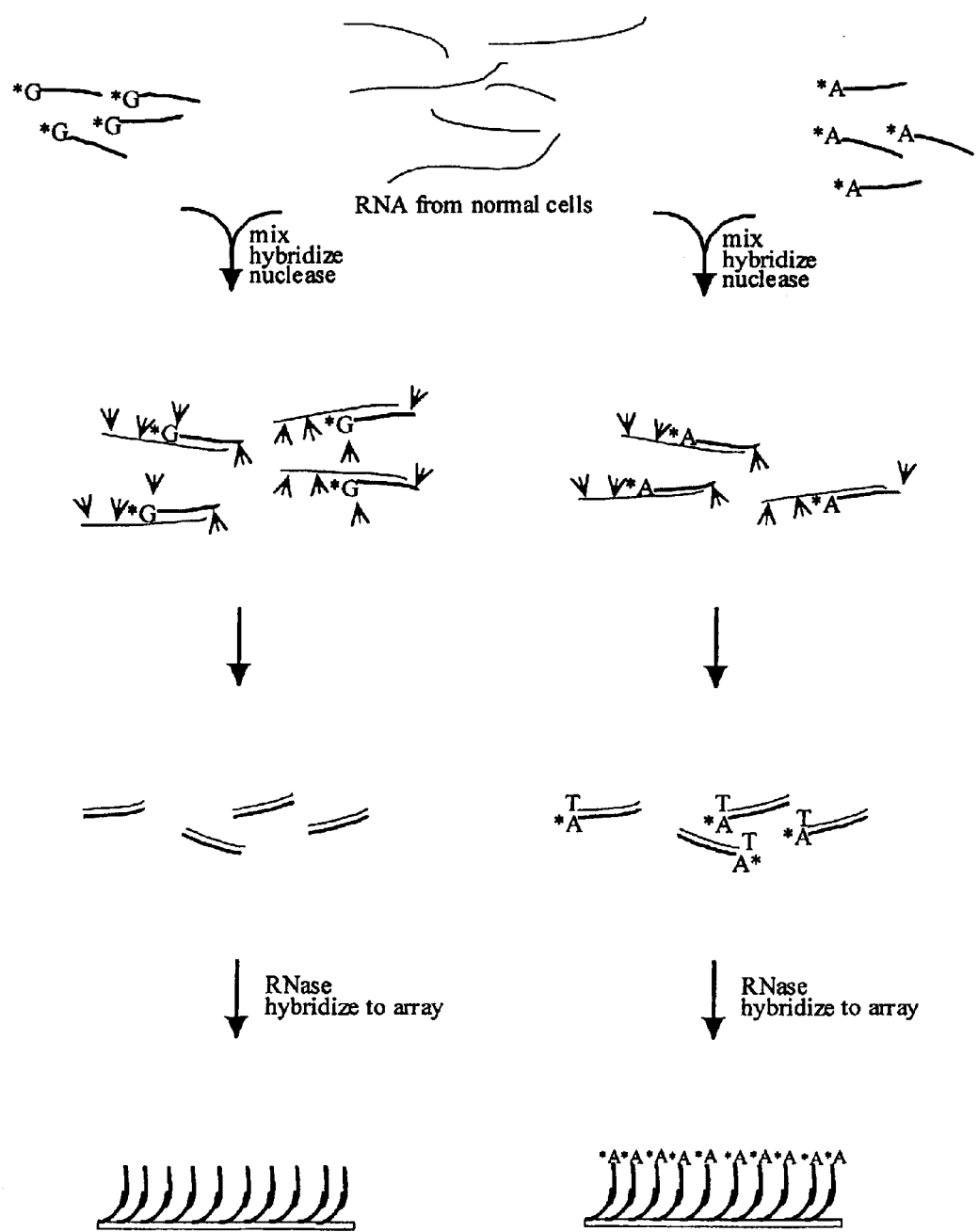
FIG. 7A depicts one aspect of the present invention, in which mutations or SNPs are detected by hybridization of an end-labeled DNA probe to a survey population of RNA molecules from normal cells, followed by nuclease treatment and hybridization of the probe to an array.
Figure 7B:
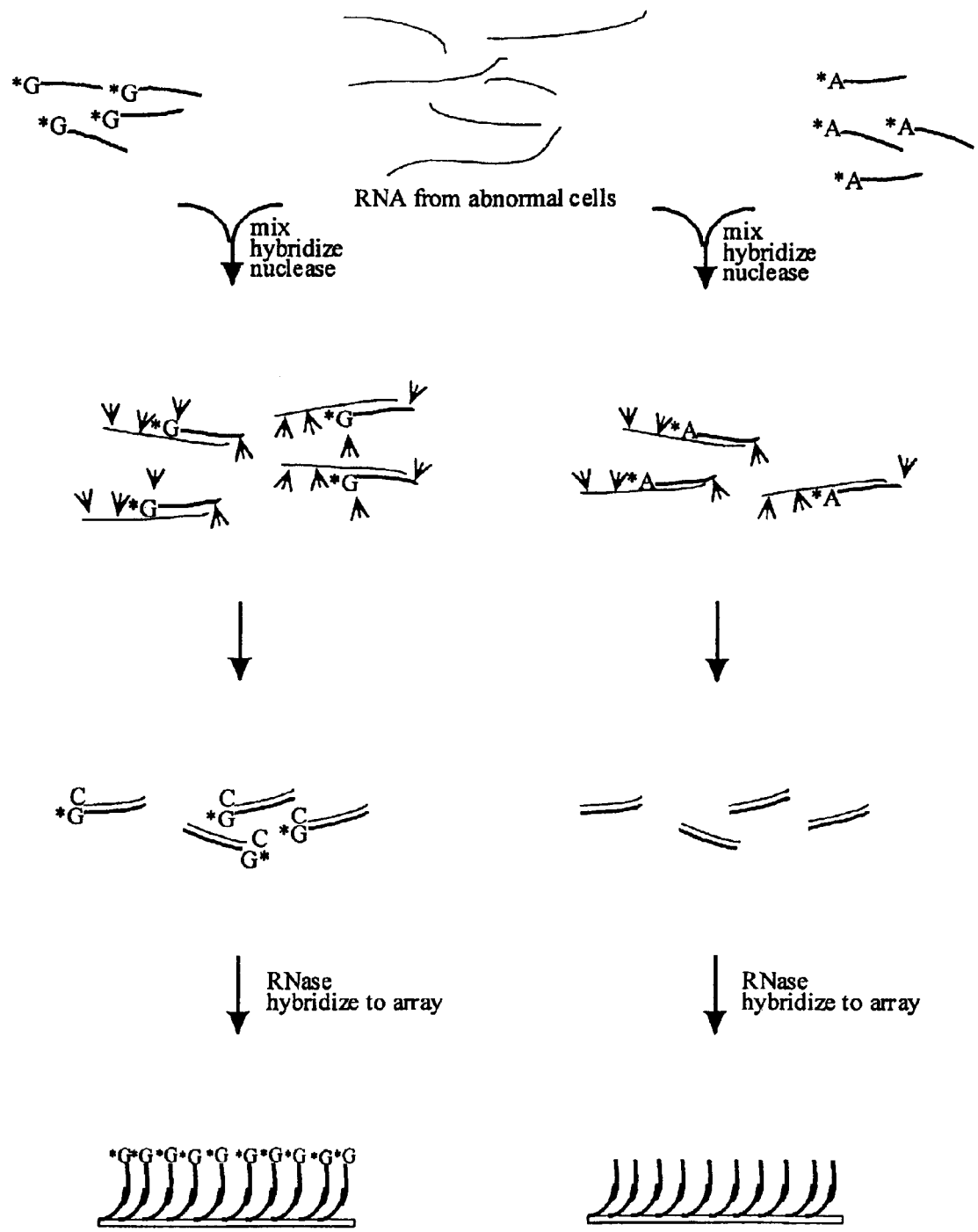
FIG. 7B depicts one aspect of the present invention, in which mutations or SNPs are detected by hybridization of an end-labeled DNA probe to a survey population of RNA molecules from abnormal cells, followed by nuclease treatment and hybridization of the probe to an array.

In the embodiment depicted in FIGS. 7A and 7B, the survey population is RNA from normal cells (FIG. 7A) or abnormal cells (FIG. 7B). The set of probe nucleic acid molecules terminate at a known or suspected mutation or SNP site, and the nucleotide at the known or suspected mutation or SNP site is labeled. From one to four different probes can be used for each mutation or SNP to be detected, such that each different probe terminates in a different labeled nucleotide, and each different labeled nucleotide is labeled with a distinct detectable label. For example, G can be labeled with Cy3, A can be labeled with Cy5, etc. In this embodiment, the probes are at least partially complementary or at least partially substantially complementary to the attached nucleic acid molecules that are bound to the array, and are at least partially complementary or at least partially substantially complementary to at least one nucleic acid molecule of the survey population. The probe nucleic acid molecules are contacted with the survey nucleic acid molecules under conditions that promote hybridization between complementary nucleic acids, and then the probe-survey population of nucleic acid molecules is contacted with, for example, Mung Bean nuclease, a single-strand specific nuclease, such that single-stranded nucleic acid molecules are digested. Because the probes terminate in known or suspected mutation or SNP sites, their labeled termini may or may not be complementary to sequences in the survey population of nucleic acid molecules, and may or may not be digested by a single-stranded nuclease. If a probe sequence at a known or suspected mutation or SNP site is not complementary to a sequence in the survey population, the labeled SNP nucleotide will be cleaved off of the probe nucleic acid molecule. If a probe sequence at a known or suspected mutation or SNP site is complementary to a sequence in the survey population, the labeled SNP nucleotide will remain on a probe nucleic acid molecule. Following nuclease treatment, the nuclease is inactivated, for example by addition of EDTA. The protected survey population nucleic acid molecules are removed, for example by digestion with RNAse, and the probe nucleic acid molecules are hybridized to the array. A positive signal on the array is indicative of a particular nucleotide at the site of the known or suspected SNP or mutation in a nucleic acid of the survey population.

Combining or modifying elements of the forgoing embodiments are within the scope of the invention. As one example, the SNP detection method of FIG. 7 can be modified to include DNA as the survey population, where the probe comprises, in addition to an end label, a biotin label, and the biotin label can be used to capture protected complexes on avidin-coated beads. In this variation, survey population fragments are stripped off of the captured fragments to leave protected probe fragments attached to avidin-coated beads. The protected probe fragments are then stripped off of the beads for hybridization to the array.

Figure 8:
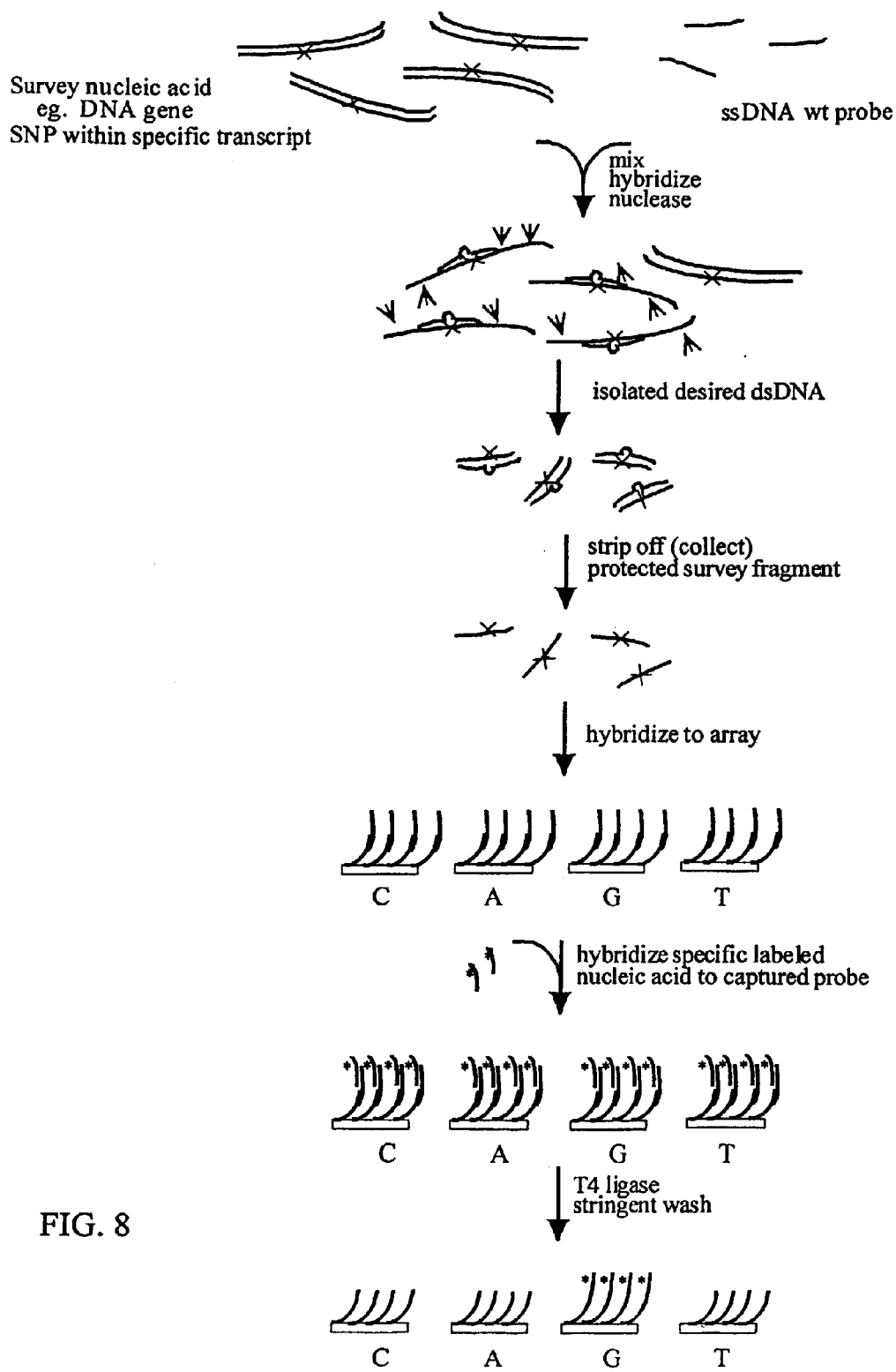
FIG. 8 depicts one aspect of the present invention, in which mutations or SNPs are detected in a population of DNA molecules by hybridization of the nucleolytic activity protected DNA fragments to an array, and subsequent ligation of a set of labeled signal nucleic acid molecules that are complementary to the protected DNA molecules to the attached nucleic acid molecules on an array.

The embodiment depicted in FIG. 8 includes a DNA survey population of nucleic acid molecules and a set of DNA probes that are complementary or substantially complementary to sequences in the survey population of nucleic acid molecules that comprise known or suspected mutation or SNP sites. The probe nucleic acid molecules are partially identical or partially substantially identical to attached nucleic acid molecules that are attached to an array, and can include specific binding members such as biotin moieties. The attached nucleic acid molecules comprise DNA and include a known or suspected mutation or SNP site occurring at least one terminus that is not attached to the array. The probe nucleic acid molecules are contacted with the survey nucleic acid molecules under conditions that promote hybridization between complementary nucleic acids, and then the probe-survey population of nucleic acid molecules is contacted with a nucleolytic activity such as Mung Bean nuclease, a single-strand specific nuclease, such that single-stranded nucleic acid molecules are digested. Following nuclease treatment, the nuclease is inactivated, for example by addition of EDTA.

The protected probe-survey population of nucleic acid molecules can then be collected by capture with streptavidin-coated beads that can bind biotinylated probe nucleic acid molecules of the protected complexes. Protected survey nucleic acid molecule fragments are stripped off the beads, using conditions that denature double-stranded DNA (e.g., basic pH), leaving the probe nucleic acid molecules attached to the beads. The protected survey nucleic acid molecules can be collected and are hybridized to attached nucleic acid molecules on a DNA array. Attached and probe nucleic acid molecules are designed such that hybridization between complementary attached and protected survey population nucleic acid molecules leaves single-stranded overhangs of protected survey population DNA molecules on the hybridized complex. The single-stranded region of the overhanging protected nucleic acid molecule strand of the hybridized complex begins at or adjacent to the mutation or SNP site, that may or may not be complementary between the protected nucleic acid molecule and the attached nucleic acid molecule, depending on the sequence of the DNA at the mutation or SNP site.

Alternatively, the probe does not comprise a specific binding member such as biotin, and after nuclease treatment and inactivation of the nuclease, protected survey nucleic acid molecules can be amplified. Preferably, amplification reactions amplify only the survey nucleic acid molecule and not the probe nucleic acid. This can be accomplished, for example, by including in the amplification reactions one or more primers that are complementary or substantially complementary to at least a portion of the survey population nucleic acid molecules, and by not including in the amplification reactions primers that are complementary or substantially complementary to at least a portion of one or more probe nucleic acid molecules.

After washing to remove unhybridized nucleic acid molecules, a set of signal nucleic acid molecules is hybridized to the array. The signal nucleic acid molecules are identical to portions of the probe nucleic acid molecules that are not identical to the attached nucleic acid molecules. In other words, signal nucleic acid molecules are designed to be at least partially complementary or at least partially substantially complementary to a portion of a survey nucleic acid molecule that can be protected by a probe nucleic acid molecule. Protected survey population molecules are in one region complementary or substantially complementary to attached nucleic acid molecules, and in another region complementary or substantially complementary to signal nucleic acid molecule.

The signal nucleic acid molecules are ligated to the attached nucleic acid molecules. A ligation is successful only if an attached nucleic acid molecule and a protected survey population nucleic acid molecule are complementary at a known or suspected SNP or mutation site. Signal nucleic acid molecules are labeled with a detectable label, such that each signal nucleic acid molecule gives rise to a signal of the same or comparable intensity. After washing under conditions that denature double-stranded DNA, the array is scanned. Detection of label at a position on the array is indicative of ligation of the signal molecule to the attached molecule at that position, which only occurs if there is exact complementarity between attached and protected survey population nucleic acid molecules.

In other embodiments of the invention, the methods of the present invention may be directed toward detecting the presence of a particular organism in a sample. For example, a sample, such as a biological sample, such as a blood sample, or an environmental sample, such as a food or water sample, may be tested for the presence of a bacteria, virus, or other microorganism using the methods of the present invention.

Components of Embodiments of the Invention

Probe Nucleic Acid Molecules

A probe nucleic acid molecule can be RNA, DNA, or partially comprised of RNA and partially comprised of DNA. It is also within the scope of the present invention to have probe nucleic acid molecules comprising nucleic acids in which the backbone sugar is other than ribose or deoxyribose; for example, certain hexoses may be substituted. Probe nucleic acids can also be peptide nucleic acids.

Probe nucleic acid molecules of the present invention can have nucleoside linkages other than the phosphodiester linkages found in naturally occurring nucleic acids. For example, two or more of their nucleoside subunits can be connected by phosphorus linkages including phosphodiester, phosphorothiate, 3'-(or -5') deoxy-3'-(or 5') thio phosphorothioate, phosphorodithioate, phophoroselenates, 3'-(or -5) deoxy phophinates, borano phosphates, 3'-(or -5') deoxy-3'-(or -5'-) amino phosphoramidates, hydrogen phosphonates, methylphosphonates, borano phosphate esters, phosphoramidates, alkyl or aryl phosphonates and phosphotriester phosphorus linkages. Alternatively or in addition, probe nucleic acids of the present invention can have two or more of their nucleoside subunits connected by carbonate, carbamate, silyl, sulfur, sulfonate, sulfonamide, formacetal, thiofromacetal, methylenedimethylhydrazo or methylimino linkages.

A probe nucleic acid molecule can comprise natural or non-naturally occurring nucleobases, for example, adenine, guanine, cytosine, uridine and thymine, as well as inosine, xanthine, hypoxanthine, 2-aminoadenine, 6-methyl and other alkyl derivatives of adenine and gaunine, 2-propyl and other alkyl derivatives of adenine and guanine, 5-halo uracil and cytosine, 5-propynyl uracil and cytosine, 6azo uracil, cytosine, and thymine, 5-uracil (pseudouracil, 4-thiouracil, 8-halo, amino, thiol, thioalkyl, hydroxyl, and other 8-substituted adenines and guanines, 5-trifluoromethyl and other 5-substituted uracils and cytosines, 7-methylguanine. Further purines and purimidines include those disclosed in U. S. Pat. No. 3,687,808 and disclosed in the Concise Encyclopedia of Polymer Science and Engineering (1990) Kroschwitz, J. I. ed., John Wiley and Sons, pages 858–859, and those disclosed by Englisch et al. (1991) Angewandte Chemie, International Edition, 30: 613.

Probe nucleic acid molecules of the present invention can be of any length, but preferably are between 5 and 500 nucleoside subunits in length, more preferably between 10 and 250 nucleoside subunits in length, and most preferably between 20 and 100 nucleoside subunits in length.

At least one of the probe nucleic acid molecules of the present invention is preferably at least partially complementary, or at least partially substantially complementary, to one or more nucleic acid molecules that are known to be present or are suspected of being present in a survey population of nucleic acids. Probe nucleic acid molecules of the present invention are preferably at least partially single-stranded. Preferably, at least a portion of a probe nucleic acid molecule that is complementary to a nucleic acid molecule that is known to be or suspected of being present in the survey population is provided in the single-stranded state. Double-stranded nucleic acid molecules may be converted to the single-stranded or partially single-stranded state for use as probes, for example by denaturation of double-stranded molecules, or by treatment of the double-stranded nucleic acid molecules with nucleases or polymerases. Preferably, at least one of the nucleoside linkages in a probe nucleic acid molecule is sensitive to cleavage by a nucleolytic agent when the probe nucleic acid molecule or portion thereof is in the single stranded state, but is not sensitive to cleavage by a nucleolytic agent when the probe nucleic acid molecule is in the double stranded state, such as when hybridized to a nucleic acid molecule that is at least partially complementary or at least partially substantially complementary.

Probe nucleic acid molecules of the present invention can be at least partially complementary or at least partially substantially complementary to an attached nucleic acid molecule of the present invention. In some preferred embodiments of the present invention, such as those depicted in FIGS. 1A, 2, 3, 4, 5, 7A, and 7B, one or more probe nucleic acid molecules can be at least partially complementary or partially substantially complementary to a nucleic acid molecule known to be present or suspected of being present in the survey population, and can also be at least partially complementary or partially substantially complementary to one or more attached nucleic acid molecules. In these embodiments, at least a portion of a probe nucleic acid molecule that is complementary or substantially complementary to a nucleic acid molecule known to be present or suspected of being present in the survey population is also complementary or substantially complementary to an attached nucleic acid molecule of the present invention.

In other embodiments of the present invention, such as those depicted in FIGS. 1B, 6A, and 6B, one or more probe nucleic acid molecules can be at least partially complementary or partially substantially complementary to a nucleic acid molecule known to be present or suspected of being present in the survey population, and can also be at least partially identical or partially substantially identical, to one or more attached nucleic acid molecules of the present invention. In these embodiments, preferably at least a portion of a nucleic acid molecule that is complementary or substantially complementary to a nucleic acid molecule known to be present or suspected of being present in the survey population is also at least partially identical or substantially identical to an attached nucleic acid molecule of the present invention.

In some preferred embodiments of the present invention directed to mutation or SNP detection, such as that depicted in FIG. 6A, one or more probe nucleic acid molecules can be partially identical or partially substantially identical to one or more attached nucleic acid molecules, and at least partially complementary or partially substantially complementary to a nucleic acid molecule known to be present or suspected of being present in the survey population. In this embodiment, at least a portion of the probe nucleic acid molecule that is complementary or substantially complementary to a nucleic acid molecule known to be present or suspected of being present in the survey population is also identical or substantially identical to an attached nucleic acid molecule of the present invention, and at least a portion of the probe nucleic acid molecule that is complementary or substantially complementary to a nucleic acid molecule know to be present or suspected of being present in the survey population is not identical or substantially identical to an attached nucleic acid molecule of the present invention. Preferably, the portions of the probe nucleic acid molecule that are identical or substantially identical to an attached nucleic acid molecule and that are not identical or substantially identical to an attached nucleic acid molecule are adjacent. Preferably, the border between the identical and non-identical portions is a known or suspected mutation or SNP.

In other embodiments of the present invention directed to mutation and SNP detection, such as that depicted in FIG. 6B, a portion of a probe nucleic acid molecule of the present invention can be identical, or substantially identical, to one or more attached nucleic acid molecules of the present invention. One or more probe nucleic acid molecules can be at least partially complementary, or at least partially substantially complementary, to at least one nucleic acid molecule known to be or suspected of being in the survey population, and can be at least partially identical, or at least partially substantially identical, to one or more attached nucleic acid molecules of the present invention. In this embodiment, at least a portion of the probe nucleic acid molecule that is complementary or substantially complementary to a nucleic acid molecule known to be present or suspected of being present in the survey population is also identical or substantially identical with the attached nucleic acid molecule of the present invention.

In this embodiment, the probe nucleic acid molecule optionally comprises a specific binding member, such as biotin, that can be used for capture of nucleolytic acitivity-protected probe-survey nucleic acid complexes. Such capture can be on a column, for example a column comprising a matrix comprising avidin. Alternatively, capture can be accomplished using magnetic beads, for example, magnetic beads coated with avidin or streptavidin. Nucleolytic activity-protected survey population nucleic acid molecules can be stripped off of captured protected complexes, for example with low salt buffers, for hybridization to an array.

Probes comprising a binding member such as, but not limited to, biotin, or comprising a nucleic acid sequence that comprises nucleolytic activity-resistant linkages that can be used for sequence specific capture of the probe, can be useful in other embodiments of the invention as well (for example, the embodiment depicted in FIG. 8) where it is desirable to capture the probe and/or nucleolytic activity-protected complexes.

Probe nucleic acid molecules can be made by synthetic methods as they are known or developed in the art, such as solid phase synthesis (see, for example, Oligonucleotide Synthesis, A Practical Approach (1984) Ed. M. J. Gait, IRL Press; "Oligonucleotides and Analogs, A Practical Approach (1991) Ed., F. Eckstein, IRL Press; Martin (1995) Helv. Chim. Acta, 78: 486–504; Beaucage and Iyer (1992) Tetrahedron 48: 2223–2311; and Beaucage and Iyer (1993) Tetrahedron 49: 6123–6194). Alternatively, probe nucleic acids can be made by reverse transcription of RNA using reverse transcriptases such as, but not limited to, Molony-Murine Leukemia Virus MMLV reverse transcriptase or Avian reverse transcriptase, or derivatives thereof, or by synthesis of RNA from DNA templates using polymerases such as T7 RNA polymerase, T3 RNA polymerase, SP6 RNA polymerase, or other RNA polymerases as they are known or developed in the art, or probe nucleic acids can be made by synthesis of DNA from DNA templates using DNA polymerases, such as but not limited to, DNA polymerase I, Klenow fragment, Taq DNA polymerase, T7 DNA polymerase, or T4 DNA polymerase. The DNA template used for synthesizing DNA or RNA probe nucleic acid molecules can be in the context of a construct, such as a plasmid construct, or can be naturally-occurring DNA isolated from an organism. Probe nucleic acid molecules can also be obtained by fragmentation of naturally occurring DNA or RNA, for example, by isolating DNA from an organism and shearing it or digesting it with restriction enzymes or nucleases. DNA or RNA isolated from an organism or sample either for direct use as probe nucleic acid molecules or for use as a template to synthesize probe nucleic acid molecules can be highly purified or only partially purified. All or only a portion of the DNA or RNA isolated from the organism can be used as probe nucleic acid molecules, or used as a template for the synthesis of probe nucleic acid molecules.

A probe nucleic acid molecule can optionally include a detectable label. Preferred labels include fluorochromes, such as Cy-3 and Cy-5, fluorescein, rhodamine, 7-amino-4-methylcoumarin, dansyl chloride, Hoescht 33258, R-phycoerythrin, Quantum Red (TM), Texas Red, green fluorescent protein (GFP) or other fluorescent labels as they are known or developed in the art. Alternatively, probe nucleic acid molecules of the present invention can be labeled with a radioisotope, such as $^{33}P$, $^{35}S$, $^{3}H$, $^{32}P$, $^{125}I$, or $^{131}I$. Other detectable labels that can be incorporated into a probe of the present invention include specific binding members that can be detected by other molecules that can generate a detectable signal, such as biotin. Enzymes that generate detectable signals in the presence of a suitable substrate, such as, but not limited to, alkaline phosphatase, luciferase, horeseradish peroxidase, and urease can also be used as labels. Labels can optionally include mass-modified bases, that aid in distinguishing nucleic acid molecules by mass spectrometry.

Such labels can be attached to or incorporated into nucleotides that are incorporated into the probe nucleic acid molecules during synthesis. Labels can also be attached to oligonucleotides after synthesis. Methods of labeling oligonucleotides are well-known in the art. See, for example, Sinha and Strepeke, "Oligonucleotides with Reporter Groups Attached to the 5' Terminus" in Oligonucleotides and Analogues: A Practical Approach, Eckstein, ed, IRL Oxford, 1991; Sinha and Cook, Nucleic Acids Res. 1988 16: 2659; Haugland, Molecular Probes Handbook of Fluorescent Probes and Research Chemicals, Molecular Probes, Inc., Eugene, Oreg. (1992) 20; Thiesen, et al., Tertrahedron Letters (1992) 33:3036; Rosenthal and Jones, Nucleic Acids Res. (1990) 18: 3095; Smith et al., Nucleic Acids Res. (1985) 13: 2399.

Survey Population of Nucleic Acid Molecules

The survey population of nucleic acid molecules can be comprised of RNA, of DNA, or of a combination of DNA and RNA. The DNA or RNA can be isolated from at least one cell, at least one tissue, at least one biological sample, at least one organism, or at least one environmental sample. A cell can be a prokaryotic or eukaryotic cell, and can be a cell isolated from an organism or a cell grown in vitro. A tissue can be an organ or cell type, including skin, hair, and blood. A biological sample can be a blood sample, a semen sample, sputum sample, a urine sample, a fecal sample, a saliva sample, a biopsy sample, an autopsy sample, or a sample from a culture or collection of organisms. Environmental samples include soil and water samples, as well as food and beverage samples, and samples and extracts from materials such as fabric, utensils, and fossilized materials.

Nucleic acids can be isolated from biological or environmental samples using methods known in the art and will depend upon the source of the material comprising the survey population of nucleic acid molecules.

Attached Nucleic Acid Molecules

An attached nucleic acid molecule is a nucleic acid molecule that is bound to a solid support. Preferably the attached nucleic acid molecule is irreversibly covalently bound to the solid support, although this is not a requirement of the present invention.

An attached nucleic acid molecule can be RNA, DNA, or partially comprised of RNA and partially comprised of DNA. It is also within the scope of the present invention to have attached nucleic acid molecules comprising nucleic acids in which the backbone sugar is other than ribose or deoxyribose; for example, certain hexoses may be substituted. Attached nucleic acids can also be peptide nucleic acids.

Attached nucleic acid molecules of the present invention can have two or more of their nucleoside subunits connected by phosphorus linkages including phosphodiester, phosphorothioate, 3'-(or -5') deoxy-3'-(or 5') thio phosphorothioate, phosphorodithioate, phophoroselenates, 3'-(or -5') deoxy phophinates, borano phosphates, 3'-(or -5') deoxy-3'-(or -5'-) amino phosphoramidates, hydrogen phosphonates, borano phosphate esters, phosphoramidates, alkyl or aryl phosphonates and phosphotriester phosphorus linkages. Alternatively or in addition, attached nucleic acids of the present invention can have two or more of their nucleoside subunits connected by carbonate, carbamate, silyl, sulfur, sulfonate, sulfonamide, formacetal, thiofromacetal, methylenedimethylhydrazo or methyleneoxymethylimino linkages. Attached nucleic acid molecules of the present invention can comprise at least one nucleolytic activity-resistant linkage, such as, but not limited to, one or more phosphorothioate, methyl phosphonate, or borano-phosphate linkages.

An attached nucleic acid molecule can comprise natural or non-naturally occurring nucleobases, for example, adenine, guanine, cytosine, uridine and thymine, as well as inosine, xanthine, hypoxanthine, 2-aminoadenine, 6-methyl and other alkyl derivatives of adenine and gaunine, 2-propyl and other alkyl derivatives of adenine and guanine, 5-halo uracil and cytosine, 5'-propynyl uracil and cytosine, 6-azo uracil, cytosine, and thymine, 5-uracil (pseudouracil, 4-thiouracil, 8-halo, amino, thiol, thioalkyl, hydroxyl, and other 8-substituted adenines and guanines, 5-trifluoromethyl and other 5-substituted uracils and cytosines, 7-methylguanine. Further purines and pyrimidines include those disclosed in U.S. Pat. No. 3,687,808 and disclosed in the Concise Encyclopedia of Polymer Science and Engineering (1990) Kroschwitz, J. I. ed., John Wiley and Sons, pages 858–859, and those disclosed by Englisch et al. (1991) Angewandte Chemie, International Edition, 30: 613.

Attached nucleic acid molecules of the present invention can be of any length, but preferably are between 5 and 500 nucleoside subunits in length, more preferably between 10 and 250 nucleoside subunits in length, and most preferably between 20 and 100 nucleoside subunits in length.

Attached nucleic acid molecules of the present invention are preferably at least partially single-stranded. One or more attached nucleic acid molecules of the present invention is preferably at least partially complementary, or at least partially substantially complementary, or at least partially identical, or at least partially substantially identical to at least one probe nucleic acid molecule of the present invention.

Attached nucleic acid molecules can be made by synthetic methods as they are known or developed in the art, such as solid phase synthesis ("Oligonucleotide synthesis, a practical approach" (1984) Ed. M. J. Gait, IRL Press; "Oligonucleotides and Analogs, A Practical Approach (1991) Ed., F. Eckstein, IRL Press; Martin (1995) Helv. Chim. Acta, 78: 486–504; Beaucage and Iyer (1992) Tetrahedron 48: 2223–2311; and Beaucage and Iyer (1993) 49: 6123–6194). Alternatively, attached nucleic acid can be made by reverse transcription of RNA using reverse transcriptases such as, but not limited to, Molony-Murine Leukemia Virus reverse transcriptase or Avian reverse transcriptase, or derivatives thereof, or by synthesis of RNA from DNA templates using polymerases such as T7 RNA polymerase, T3 RNA polymerase, SP6 RNA polymerase, or other RNA polymerases as they are known or developed in the art, or probe nucleic acids can be made by synthesis of DNA from DNA templates using DNA polymerases, such as but not limited to, DNA polymerase I, Klenow fragment, Taq DNA polymerase, T7 DNA polymerase, or T4 DNA polymerase. A DNA template used for synthesizing DNA or RNA attached nucleic acid molecules can be in the context of a construct, such as a plasmid construct, or can be naturally-occurring DNA isolated from an organism. Attached nucleic acid molecules can also be obtained by fragmentation of naturally occurring DNA or RNA, for example, by isolating DNA from an organism and shearing it or digesting it with restriction enzymes or nucleases. All or only a portion of the DNA or RNA isolated from the organism can be used as attached nucleic acid molecules, or used as a template for the synthesis of attached nucleic acid molecules.

An attached nucleic acid molecule can optionally include a detectable label. Preferred labels include fluorochromes, such as Cy-3 and Cy-5, fluorescein, rhodamine, 7-amino-4-methylcoumarin, dansyl chloride, Hoescht 33258, R-phycoerythrin, phycocyanin, allophycocyanin, Quantum Red (TM), Texas Red, green fluorescent protein (GFP) or other fluorescent labels as they are known or developed in the art. Alternatively, attached nucleic acid molecules of the present invention can be labeled with a radioisotope, such as $^{33}P$, $^{35}S$, $^{3}H$, $^{32}P$, $^{125}I$, or $^{131}I$. Other detectable labels that can be incorporated into an attached nucleic acid of the present invention include specific binding members that can be detected by other molecules that can generate a detectable signal, such as biotin. Enzymes that generate detectable signals in the presence of a suitable substrate, such as, but not limited to, alkaline phosphatase, luciferase, horeseradish peroxidase, and urease can also be used as labels. Labels can optionally include mass-modified bases, that aid in distinguishing nucleic acid molecules by mass spectrometry.

Such labels can be attached to or incorporated into nucleotides that are incorporated into attached nucleic acid molecules during synthesis. Labels can also be attached to oligonucleotides after synthesis. Methods of labeling oligonucleotides are well-known in the at See, for example, Sinha and Striepeke, "Oligonucleotides with Reporter Groups Attached to the 5' Terminus" in Oligonucleotides and Analogues: A Practical Approach, Eckstein, ed, IRL Oxford, 1991; Sinha and Cook, Nucleic Acids Res. 1988 16: 2659; Haugland, Molecular Probes Handbook of Fluorescent Probes and Research Chemicals, Molecular Probes, Inc., Eugene, Oreg. (1992) 20; Thiesen, et al., Tertrahedron Letters (1992) 33:3036; Rosenthal and Jones, Nucleic Acids Res. (1990) 18: 3095; Smith et al., Nucleic Acids Res. (1985) 13: 2399.

Nucleic acid molecules can be attached to solid supports simply by spotting the nucleic acids in solution onto a nylon, nitrocellulose, polycarbonate, polystyrene, or other plastic solid support. A solid support or one or more components thereof, including precursor materials of solid supports, may also be immersed in a solution of one or more nucleic acid molecules to allow the nucleic acid molecules to absorb into or onto the material. The solid support is then dried and optionally heated to fix the nucleic acids to the solid support.

Arrays having surfaces with covalently bound amine groups are commercially available (Nunc, Naperville, Ill.), and nucleic acid molecules can be coupled to these arrays using carbodiimides such as 1-ethyl-3-(3-dimethylaminopropyl)-carbodiimide as condensing reagents.

Preferably, attached nucleic acid molecules of the present invention are bound to the solid support such that their 3' termini are unbound. In this aspect, nucleic acid molecules may be attached to a solid support via their 5' termini, or may be attached to the solid support via a linker arm. Covalent attachment of nucleic acid molecules of the present invention to solid supports may be accomplished by a reaction between a reactive site or a binding moiety on the solid support and a reactive site or another binding moiety attached to the nucleic acid molecules, or can be done via linkers or spacer molecules, where the two binding moieties can react to form a covalent bond. A variety of covalent attachment functional groups may be used to attach a nucleic acid molecules to a solid support, including disulfide, carbamate, hydrazone, ester, N-functionalized thiourea, functionalized maleimide, streptavidin or avidin/biotin, mercuric-sulfide, gold-sulfide, amide, thiolester, azo, ether, and amino. For example, binding of a nucleic acid molecule to a solid support can be carried out by reacting a free amino group of an amino-modified nucleic acid molecule with the reactive imidazote carbamate of the solid support. Arrays can also be made by synthesizing nucleic acids on the solid supports, as described in U.S. Pat. Nos. 5,359,115, 5,420, 328, 5,424,186, and 5,143,854.

Solid Support

A solid support of the present invention is a solid material having a surface for attachment of molecules, compounds, cells, or other entities. A solid support can be a membrane, such as, for example, a nylon or nitrocellulose membrane, or can be a plate or dish and can be comprised of glass, ceramics, metals, or plastics, such as, for example, a 96-well plate made of, for example, polystyrene, polypropylene, polycarbonate, or polyallomer. A solid support can also be a particle or bead that can comprise glass, can comprise one or more plastics or polymers, such as, for example, polystyrene, polyacrylamide, sepaharose, agarose, cellulose or dextran, and/or can comprise metals, particularly paramagnetic metals, such as iron.

One preferred solid support of the present invention is a chip or array that comprises a flat surface, and that may comprise glass, silicon, nylon, polymers, plastics, ceramics, or metals. Nucleic acid molecules are attached to the surface, such that the attached nucleic acid molecules are preferably at least partially identical to or are at least partially complementary to identified or unidentified genes (such as expressed sequence tags (ESTs)) and are arranged on the array at known locations so that positive hybridization events may be correlated to expression of a particular gene in the physiological source from which the target nucleic acid sample is derived.

A number of different array configurations and methods for their production are known to those of skill in the art and disclosed in U.S. Pat. Nos.: 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are herein incorporated by reference.

Another preferred solid support of the present invention is a particle that comprises a spherical or nonflat surface, and that may comprise glass, polymers (such as, but not limited to, polyacrylamide, agaroses, dextrans, cellulose, or plastics), ceramics, or metals. Nucleic acid molecules can be attached to the particles, which may or may not be porous. Such particles can be used, for example, to capture nucleic acid molecules of the survey population or probe nucleic acid molecules by hybridization.

Hybridization of Probe and Survey Population

The method of the present invention includes hybridization of one or more probe nucleic acid molecules of the present invention with a survey population of nucleic acid molecules. If the survey population of nucleic acid molecules comprises double-stranded DNA, or if the nucleic acid molecules of the survey population comprise double-stranded regions, prior to the hybridization step the nucleic acid molecules of the survey population are preferably converted to the single-stranded state to promote hybridization with the nucleic acid probe.

The hybridization reaction can be done with both probe nucleic acid molecules and survey nucleic acid molecules in solution, under conditions that promote hybridization between molecules that are complementary, partially complementary, substantially complementary, or partially substantially complementary. Hybridization conditions such as the temperature of hybridization, salt concentrations, and the concentration of denaturing compounds such as formamide, can be adjusted to promote the hybridization of molecules of different degrees of complementarity. A discussion of hybridization conditions can be found in Ausubel et al. (1998) Short Protocols in Molecular Biology, John Wiley & Sons, New York, 1992. Hybridization conditions are also described in Sambrook et al., DNA Cloning, A Laboratory Manual, Cold Spring Harbor, 1989. Hybridization conditions are also described in Hybridization with Nucleic Acid Probes, Part I and Part II, Elsevier, New York and in "Molecular Biology Protocols" web-site: listeria.nwfsc.noaa.gov/protocols.html.

Contacting one or more probe nucleic acid molecules of the present invention with a survey population of nucleic acid molecules under conditions that promote hybridization between nucleic acid molecules that are at least partially complementary or substantially complementary results in a probe-survey population mixture of nucleic acid molecules. The probe-survey population mixture of nucleic acid molecules can include single-stranded nucleic acid molecules, double-stranded nucleic acid molecules, and/or nucleic acid molecules that are partially single-stranded and partially double-stranded.

Treatment with Nucleolytic Activity

The probe nucleic acid molecule-survey population nucleic acid molecule mixture of the present invention can be treated with one or more nucleolytic activities. Nucleolytic activities of the present invention can be chemical cleavage agents, such as osmium tetroxide, hydrogen peroxide, hydroxylamine, and permanganate, or can be enzymes such as nucleases. Preferred nucleases include single-strand specific nucleases, such as S1 nuclease, Mung Bean Nuclease, Rnase T1, Rnase A, or Rnase H.

For use in screening a survey population comprising RNA, nuclease protection conditions are described in Ausubel et al., Short Protocols in Molecular Biology, John Wiley & Sons, New York, 1992, Units 4.6–4.7, page 4–14 to page 4–20. Additional practical guidance on nuclease protection can be found, for example, in 2000 Catalog, Ambion, Inc., Austin, Tex.; Walmsely and Patient, "Quantitative and Qualitative Analysis of Exogenous Gene Expression by S1 Nuclease Protection Assay," Mol. Biotechnol. 1: 265–275, 1994; Lau et al., "Critical Assessment of the RNase Protection Assay as a Means of Determining Exon Sizes," Anal. Biochem. 209: 360–366, 1993; Haines and Gillispie, "RNA Abundance Measured by a Lysate RNase Protection Assay," Biotechniques 12: 736–741, 1992; and Strauss and Jacobowitz, "Quantitative Measurement of Calretinin and Beta-Actin mRNA," Brain Res. Mol. Brain Res. 20: 229–239, 1993.

Treatment with a nucleolytic activity removes nucleolytic activity-sensitive nucleic acid molecules from the probe-survey population mixture of nucleic acid molecules, resulting in a population of nucleolytic-activity-protected nucleic acid molecules. In a preferred embodiment of the present invention, treatment with a nucleolytic activity removes single-stranded nucleic acid molecules and single-stranded regions of nucleic acid molecules from the probe-survey population mixture of nucleic acid molecules, and results in a population of double-stranded nucleolytic activity-protected nucleic acid molecules. However, the present invention also contemplates that molecules may be protected from or sensitive to nucleolytic activity for reasons other than that they are double-stranded or single-stranded. For example, particular nucleic acid molecules may comprise one or more nuclease-resistant linkages that render the nucleic acid molecules or portions thereof resistant to particular nucleases.

In some embodiments of the present invention, it may be desirable to amplify nucleolytic-activity protected nucleic acid molecules. Such embodiments include embodiments directed toward the detection of contaminants or pathogens. Methods of DNA amplification are well known in the art. Amplification of RNA is known in the art as well, and generally relies on a first cDNA synthesis reaction using a reverse transcriptase. Preferably, the amplification of nucleolytic-activity protected products is linear or substantially linear, and preferably, the amplification preferentially amplifies one strand, preferably the strand that is at least partially complementary, or at least partially substantially complementary to one or more attached nucleic acid molecules of the present invention.

After treatment of the probe nucleic acid molecule-survey population nucleic acid molecule mixture with one or more nucleolytic activities, the resulting nucleolytic activity-protected nucleic acid molecules are preferably treated to inhibit or remove the nucleolytic activity. Such treatments can involve heating the nucleolytic activity-protected nucleic acid molecules, or adding reagents such as, for example, detergents or chelating agents such as EDTA, The nucleolytic activity-protected nucleic acid molecules can then be used directly, but is preferably treated with any of a variety of agents that denature nucleic acids to single-stranded form, including but not limited to, high temperature, high pH, denaturing agents, or nucleases. For example, in certain preferred embodiments the nucleolytic activity-protected nucleic acid molecules are treated with a second nuclease in order to provide the protected probe nucleic acid molecules or fragments thereof or protected fragments of the survey population of nucleic acid molecules in single-stranded form for hybridization to the attached nucleic acid molecules on the solid support. Nucleases can be selected based on their ability to degrade one of the strands of the nucleic acids of the nucleolytic-activity-protected nucleic acid molecules and to leave the strands that are to be hybridized to the attached nucleic acids of the solid support intact. For example, in embodiments where at least one probe is at least partially complementary, or at least partially substantially complementary, to one or more attached nucleic acid molecules, and the probe or probes comprise DNA and the survey population comprises RNA, the probe or probes can be rendered single stranded by treatment of the probe-survey population of nucleic acid molecule mixture with Dnase-free Rnase, such as Rnase H.

Hybridization to Solid Support

The nucleolytic activity-protected nucleic acid molecules or single-stranded portions thereof are contacted with the array under conditions sufficient for hybridization of nucleic acids to occur to form attached nucleic acid molecule/nucleolytic activity-protected nucleic acid molecule complexes. Suitable hybridization conditions are well known to those of skill in the art and reviewed in Maniatis et al, supra and WO 95/21944, where the conditions can be modulated to achieve a desired specificity in hybridization, e.g. highly stringent or moderately stringent conditions. For example, low stringency hybridization conditions may be at 50 degress C. and 6 times SSC (0.9 M sodium chloride/0.09 M sodium citrate) while hybridization under stringent conditions may be at 50 degress C. or higher and 0.01 times SSC (15 mM sodium chloride/1.5 mM sodium citrate).

In many instances, it is desirable to include in the sample of nucleolytic-activity-protected nucleic acid molecules that is contacted with the array an unlabeled or labeled set of standard DNA molecules that are present in known amounts and can be used as calibrating agents in subsequent analysis. Standard DNA molecules may simply be added to the nucleic acids to be contacted with the array. Alternatively, one or more standards can be provided in the survey population of nucleic acid molecules, and the standard or standards will be designed such that they are complementary or not complementary to one or more probe nucleic acid molecules.

Following hybridization, a washing step can be employed to remove unhybridized nucleolytic-activity-protected nucleic acid molecules from the solid support. A variety of wash solutions and protocols for their use are known to those of skill in the art and may be used.

Labeling of Hybridized to Complexes on Solid Support

In certain preferred embodiments of the present invention (such as those illustrated in FIGS. 1A, 1B, 6A, and 6B), attached nucleic acid molecule/nucleolytic activity-protected nucleic acid molecule complexes are labeled by using one or more polymerases and one or more labeled nucleotides.

Preferably, hybridization of an attached nucleic acid molecule and a nucleolytic activity-protected molecule occurs such that only a portion of the nucleolytic activity-protected nucleic acid molecule hybridizes to an attached nucleic acid molecule, such that a nucleolytic activity-protected nucleic acid molecule in a hybridized complex is partially single-stranded and partially double-stranded. This allows the unhybridized portion of a nucleolytic activity-protected nucleic acid molecule in a hybridized complex to act as a template and the hybridized portion of an attached nucleic acid molecule in a hybridized complex to be used as a primer in polymerase reactions that extend the attached nucleic acid molecule of an attached nucleic acid molecule/nucleolytic activity-protected nucleic acid molecule complex. In the alternative, hybridization of a nucleolytic activity-protected nucleic acid molecule and an attached nucleic acid molecule occurs such that only a portion of the attached nucleic acid hybridizes to a nucleolytic activity-protected nucleic acid molecule, such that a hybridized attached nucleic acid molecule in a hybridized complex is partially single-stranded and partially double-stranded. This allows the unhybridized portion of an attached nucleic acid molecule in a hybridized complex to act as a template and the hybridized portion of a nucleolytic activity-protected nucleic acid molecule in a hybridized complex to act as a primer in polymerase reactions that extend the nucleolytic activity-protected nucleic acid molecule of an attached nucleic acid molecule/nucleolytic activity-protected nucleic acid molecule complex. It is also within the scope of the present invention to extend both an attached nucleic acid molecule and a nucleolytic activity-protected nucleic acid molecule of a hybridized complex using one or more polymerases, in one or more polymerase reactions performed simultaneously or in series.

It may be preferred in particular embodiments (especially, but not restricted to, embodiments directed toward mutation and SNP detection) to extend only one of the strands of a nucleic acid molecule of the hybridized complex. That is, it can be preferable to extend either the nuclcolytic activity-protected nucleic acid molecule strand of the hybridized complex or the attached nucleic acid molecule strand of the hybridized complex, but not both). There are several ways of accomplishing this, some of which are discussed as follows. First, attached nucleic acid molecules and probe nucleic acid molecules can be designed such that hybridization between an attached nucleic acid molecule and a nucleolytic activity-protected nucleic acid molecule occurs such that only one of the two nucleic acid molecules;has a single-stranded overhang region in the hybridized complex. Second, the attached nucleic acid molecules and probe nucleic acid molecules can comprise different nucleic acids, such that one of the strands of a hybridized complex comprises DNA and the other strand of a hybridized complex comprises RNA. In this case, one or more polymerases is provided that is specific for synthesis of either DNA or RNA, but not both. A third option is to use either probe nucleic acid molecules or attached nucleic acid molecules that comprises moieties at their 3' ends that do not permit extension of the nucleic acid molecules, such as, but not limited to dideoxy nucleotides. A fourth possibility is to design probe nucleic acid molecules and attached nucleic acid molecules such that one end of a hybridizing complex does not base pair at the terminal base of the non-overhanging nucleic acid. Lack of precise base pairing precludes extension of the nucleic acid strand with polymerases.

Examples of DNA polymerases useful in the present invention include, but are not limited to, DNA Polymerase I, Klenow fragment, T4 DNA Polymerase, T7 DNA polymerase, *T. aquaticus* ("Taq") DNA polymerase, and reverse transcriptases. Polymerase reactions are performed with nucleotides, at least one of which is detectably labeled. Labels can be enzymes, specific binding members, radioisotopes, or fluorochromes. Preferred labels are $^{33}$P and fluorochromes such as Cy3 and Cy5. Additional reagents such as buffering agents, salts, etc. can be provided to optimize the polymerase reactions. Polymerase reactions for incorporating labeled nucleotides may be performed at varying temperatures, depending on the polymerases used and their activity and specificity at particular temperatures.

A preferred feature of the embodiments that include labeling of hybridized complexes on a solid support and that are directed toward expression profiling is that each hybridization event with a particular species of label results in a signal of the same intensity. Preferably, all four nucleotides are detectably labeled, and the number of bases to be polymerized in the extension of the nucleolytic activity-protected molecule is uniform among all the attached nucleic acid molecule/nucleolytic activity-protected complexes of the array. That is, the attached nucleic acid molecules and probe nucleic acid molecules for all positions on the array are designed such that hybridization between nucleolytic activity-protected nucleic acid molecules and attached nucleic acid molecules leaves a uniform number of bases of the nucleic acid molecules of the hybridized complexes that are not base-paired and that can be "filled in" with labeled nucleotides in polymerase reactions.

In embodiments that include labeling of hybridized complexes on a solid support and that are directed toward mutation or SNP detection (for example, those depicted in FIGS. 6A and 6B), the attached nucleic acid molecules and probe nucleic acid molecules are designed such that attached nucleic acid molecules comprise mutations or SNPs that are positioned at their unattached 3' termini and nucleolytic activity-protected nucleic acid molecules comprise mutations or SNPs that are not at their termini. Hybridization of nucleolytic activity-protected nucleic acid molecules to attached nucleic acid molecules on the solid support results in hybridized complexes comprising nucleic acids that are partially double-stranded and partially single-stranded, in which the double-stranded region terminates at a known or suspected mutation or SNP site. The mutation or SNP site is therefore the site where a polymerase would initiate nucleic acid synthesis. If an attached nucleic acid molecule can base pair with a nucleolytic activity-protected nucleic acid molecule at the mutation or SNP site, labeled nucleotides can be incorporated in polymerase reactions. If, however, the mutation or SNP sequence of the attached nucleic acid molecule and the nucleolytic activity-protected molecule are not complementary, the polymerase cannot incorporate nucleotides. The detection of label at an array site therefore identifies the attached nucleic acid molecule at that array site as complementary to the mutation or SNP sequence in a member of the survey population of nucleic acid molecules, and thereby identifies a mutation or SNP in a survey population of nucleic acid molecules.

In this embodiment, all four nucleotides can optionally be labeled to ensure that label is incorporated into attached nucleic acid molecule/nucleolytic activity-protected nucleic acid molecules complexes when the polymerase reaction is successful.

In a related embodiment, the survey population of nucleic acid molecules can be RNA or DNA, and the probe nucleic acid molecule is at least partially identical, at least partially substantially identical, at least partially complementary, or at least partially substantially complementary to one or more attached nucleic acid molecules. Attached nucleic acid molecule/nucleolytic activity-protected nucleic acid molecule complexes are labeled by using one or more polymereses and one or more labeled nucleotides. Preferably, hybridization of an attached nucleic acid molecule and a nucleolytic activity-protected molecule occurs such that the nucleolytic-activity-protected nucleic acid molecule hybridizes to only a portion of an attached nucleic acid molecule, such that a hybridized attached nucleic acid molecule is partially single-stranded and partially double-stranded. This allows the hybridized portion of the nucleolytic activity-protected nucleic acid molecule to act as a primer and the unhybridized single-stranded portion of an attached nucleic acid molecule to be used as a template in polymerase reactions that extend the nucleolytic activity-protected nucleic acid molecule. Examples of DNA polymerases useful in the present invention include but are not limited to, DNA Polymerase I, Klenow fragment, T4 DNA Polymerase, T7 DNA polymerase, *T. aquaticus* DNA polymerase, and reverse transcriptases.

An important feature of this embodiment of the invention is that the nucleolytic activity-protected nucleic acid molecules and attached nucleic acid molecules are designed such that nucleolytic activity-protected nucleic acid molecules comprise mutations or SNPs that are not at their termini and attached nucleic acid molecules terminate just before mutation or SNP sites at their unattached 3' termini. Hybridization of nucleolytic activity-protected nucleic acid molecules to attached nucleic acid molecules on the solid support results in nucleolytic activity-protected nucleic acid molecules that are partially double-stranded and partially single-stranded, in which the double-stranded region terminates adjacent to a known or suspected mutation or SNP. The incorporation of a terminating nucleotide with a distinguishing label at the mutation or SNP postion identifies the sequence of the mutation or SNP. Polymerase reactions are performed with terminating nucleotides, such as dideoxynucleotides, at least one of which is detectably labeled. Terminating nucleotides do not permit the incorporation of additional nucleotides into a growing nucleic acid polymer. At least one terminating nucleotide is detectably labeled. Preferably, all four nucleotides are detectably labeled with different distinguishable labels. Labels can be enzymes, specific binding members, radioisotopes, or fluorochromes. Preferred labels are fluorochromes such as Cy3 and Cy5. Additional reagents such as buffering agents, salts, etc. can be provided to optimize the polymerase reactions.

Use of End-labeled Probes

In another embodiment of the invention, depicted in FIGS. 7A and 7B, nucleic acid probes of the present invention can comprise a mutation or SNP and are labeled at least one terminus, where the terminating nucleotide that is labeled occurs at a mutation or SNP site. In this embodiment, a probe nucleic acid molecule is at least partially complementary, or at least partially substantially complementary to one or more attached nucleic acid molecules of the present invention. The survey population of nucleic acid molecules can be DNA, but is preferably RNA. Following hybridization of the survey population of nucleic acid molecules and one or more probe nucleic acid molecules, nuclease treatment with single-strand specific nucleases removes single stranded nucleic acids, including the labeled terminal nucleotide of the probe, if it does not hybridize to a known or suspected mutation or SNP. Nucleolytic activity-protected probe nucleic acid molecules are hybridized to the attached nucleic acid molecules on a solid support. Only probe nucleic acid molecules that are complementary to known or suspected mutations or SNPs at their terminal nucleotides will result in a signal on the array. In this embodiment, from one to four probes, each terminating in a different labeled nucleotide, can be hybridized to different arrays.

Hybridization of Signal Nucleic Acid Molecules to Hybridized Complexes on Solid Support In certain embodiments of the present invention, such as those illustrated in FIGS. 4 and 8, one or more signal nucleic acid molecules can be hybridized to the attached nucleic acid molecule/nucleolytic activity-protected nucleic acid molecule complexe. In this embodiment, a "sandwich" hybridization is performed, in which nucleolytic activity-protected nucleic acid molecules are hybridized to attached nucleic acid molecules to form hybridized complexes, and signal nucleic acid molecules are hybridized to nucleolytic activity-protected nucleic acid molecules in hybridized complexes. One or more signal nucleic acid molecules can be at least partially complementary, at least partially substantially complementary, at least partially identical, or at least partially substantially identical to at least one probe nucleic acid molecule. Thus, at least a portion of at least one nucleolytic activity-protected nucleic acid molecule is at least partially complementary, or at least partially substantially complementary to at least a portion of one or more signal nucleic acid molecules. Preferably, the region of the nucleolytic activity-protected nucleic acid molecule that is complementary to at least a portion of a signal nucleic acid molecule is a region that is not complementary to an attached nucleic acid molecule of the present invention.

A signal nucleic acid molecule can be RNA, DNA, or partially comprised of RNA and partially comprised of DNA. It is also within the scope of the present invention to have signal nucleic acid molecules comprising nucleic acids in which the backbone sugar is other than ribose or deoxyribose; for example, certain hexoses may be substituted. Signal nucleic acids can also be peptide nucleic acids.

A signal nucleic acid molecules of the present invention can have nucleoside linkages other than the phosphodiester linkages found in naturally occurring nucleic acids. For example, two or more of their nucleoside subunits can be connected by phosphorus linkages including phosphodiester, phosphorothiate, 3'-(or -5') deoxy-3'-(or 5') thio phosphorothioate, phosphorodithioate, phophoroselenates, 3'-(or -5') deoxy phophinates, borano phosphates, 3'-(or -5') deoxy-3'-(or -5'-) amino phosphoramidates, hydrogen phosphonates, methylphosphonates, borano phosphate esters, phosphoramidates, alkyl or aryl phosphonates and phosphotriester phosphorus linkages. Alternatively or in addition, the signal nucleic acids of the present invention can have two or more of their nucleoside subunits connected by carbonate, carbamate, silyl, sulfur, sulfonate, sulfonamide, formacetal, thiofromacetal, methylenedimethylhydrazo or methylimino linkages.

A signal nucleic acid molecule can comprise natural or non-naturally occurring nucleobases, for example, adenine, guanine, cytosine, uridine, and thymine, as well as inosine, xanthine, hypoxanthine, 2-aminoadenine, 6-methyl and other alkyl derivatives of adenine and gaunine, 2-propyl and other alkyl derivatives of adenine and guanine, 5-halo uracil and cytosine, 5-propynyl uracil and cytosine, 6-azo uracil, cytosine, and thymine, 5-uracil (pseudouracil, 4-thiouracil, 8-halo, amino, thiol, thioalkyl, hydroxyl, and other 8-substituted adenines and guanines, 5-trifluoromethyl and other 5-substituted uracils and cytosines, 7-methylguanine.

Further purines and purimidines include those disclosed in U.S. Pat. No. 3,687,808 and disclosed in the Concise Encyclopedia of Polymer Science and Engineering (1990) Kroschwitz, J. I. ed., John Wiley and Sons, pages 858–859, and those disclosed by Englisch et al. (1991) Angewandte Chemie, International Edition, 30: 613.

Signal nucleic acid molecules of the present invention can be of any length, but preferably are between 5 and 500 nucleoside subunits in length, more preferably between 10 and 250 nucleoside subunits in length, and most preferably between 20 and 100 nucleoside subunits in length.

Signal nucleic acid molecules of the present invention are preferably at least partially single-stranded. Preferably, at least a portion of a signal nucleic acid molecule that is complementary to a nucleolytic activity-protected nucleic acid molecule is provided in the single-stranded state. Double-stranded nucleic acid molecules may be converted to the single-stranded, or partially single-stranded, state for use as signal nucleic acid molecules, for example by denaturation of double-stranded molecules, or by treatment of the double-stranded nucleic acid molecules with nucleases or polymerases.

Signal nucleic acid molecules can be made by synthetic methods as they are known or developed in the art, such as solid phase synthesis ("Oligonucleotide synthesis, a practical approach" (1984) Ed. M. J. Gait, IRL Press; "Oligonucleotides and Analogs, A Practical Approach (1991) Ed., F. Eckstein, IRL Press; Martin (1995) Helv. Chim. Acta, 78: 486–504; Beaucage and Iyer (1992) Tetrahedron 48: 2223–2311; and Beaucage and Iyer (1993) 49: 6123–6194). Alternatively, signal nucleic acid molecules can be made by reverse transcription of RNA, or by synthesis of RNA from DNA templates using polymerases such as RNA T7 polymerase, RNA T3 polymerase, RNA SP6 polymerase, or other RNA polymerases as they are known or developed in the art, or signal nucleic acids can be made by synthesis of DNA from DNA templates using DNA polymerases, such as but not limited to, DNA polymerase I, Klenow fragment, Taq DNA polymerase, T7 DNA polymerase, or T4 DNA polymerase.

A signal nucleic acid molecule preferably includes a detectable label. Preferably all of the signal nucleic acid molecules in a set of signal nucleic acid molecules to be hybridized to attached nucleic acid molecule/nucleolytic activity-protected complexes on a solid support of the present invention are labeled to the same specific activity, such that detection of the signal nucleic acid molecule gives quantitative information of the representation of a nucleic acid sequence in the survey population.

Preferred labels include fluorochromes, such as Cy-3 and Cy-5, fluorescein, rhodamine, 7-amino-4-methylcoumarin, dansyl chloride, Hoescht 33258, R-phycoerythrin, Quantum Red (TM), Texas Red, green fluorescent protein (GFP) or other fluorescent labels as they are known or developed in the art. Alternatively, signal nucleic acid molecules of the present invention can be labeled with a radioisotope, such as $^{33}P$, $^{35}S$, $^{3}H$, $^{32}P$, $^{125}I$, or $^{131}I$. Other detectable labels that can be incorporated into a signal of the present invention include specific binding members that can be detected by other molecules that can generate a detectable signal, such as biotin. Enzymes that generate detectable signals in the presence of a suitable substrate, such as, but not limited to, alkalie phosphatase, luciferase, horeseradish peroxidase, and urease can also be used as labels. Labels can optionally include mass-modified bases, that aid in distinguishing nucleic acid molecules by mass spectrometry.

Such labels can be attached to or incorporated into nucleotides that are incorporated into the signal nucleic acid molecules during synthesis. Labels can also be attached to oligonucleotides after synthesis. Methods of labeling oligonucleotides using are well-known in the art. See, for example, Sinha and Striepeke, "Oligonucleotides with Reporter Groups Attached to the 5' Terminus" in Oligonucleotides and Analogues: A Practical Approach, Eckstein, ed, IRL Oxford, 1991; Sinha and Cook, Nucleic Acids Res. 1988 16: 2659; Haugland, Molecular Probes Handbook of Fluorescent Probes and Research Chemicals, Molecular Probes, Inc., Eugene, Oreg. (1992) 20; Thiesen, et al., Tertrahedron Letters (1992) 33:3036; Rosenthal and Jones, Nucleic Acids Res. (1990) 18: 3095; Smith et al., Nucleic Acids Res. (1985) 13: 2399.

Signal nucleic acid molecules are contacted with the array under conditions sufficient for hybridization of nucleic acids to probe to occur. Suitable hybridization conditions are well known to those of skill in the art and reviewed in Maniatis et al, supra and WO 95/21944, where the conditions can be modulated to achieve a desired specificity in hybridization, e.g. highly stringent or moderately stringent conditions. For example, low stringency hybridization conditions may be at 50 degress C. and 6 times SSC (0.9 M sodium chloride/0.09 M sodium citrate) while hybridization under stringent conditions may be at 50 degress C. or higher and 0.1 times SSC (15 mM sodium chloride/1.5 mM sodium citrate).

Following hybridization, a washing step is employed where unhybridized labeled signal nucleic acids are removed from the support surface. A variety of wash solutions and protocols for their use are known to those of skill in the art and may be used.

In the embodiment depicted in FIG. 8, following hybridization of the signal oligonucleotide to the hybridized complexes on a solid support, a ligation reaction is performed to covalently attach a signal nucleic acid molecule to an attached nucleic acid molecule. In this embodiment, attached nucleic acid molecules terminate at known or suspected mutation or SNP sites, and nucleolytic activity-protected nucleic acid molecules in hybridized complexes comprise known or suspected mutation or SNP sites that do not occur at their termini. A signal nucleic acid molecule is designed such it borders a known or suspected SNP site at one terminus, such that when hybridized to a nucleolytic activity-protected nucleic acid molecule, it abuts an attached nucleic acid molecule. The signal nucleic acid molecule can be ligated to the attached nucleic acid molecule only if there is precise complementarity between an attached nucleic acid molecule and a nucleolytic activity-protected nucleic acid molecule at the known or suspected mutation or SNP site. Ligases useful in the present invention include, but are not limited to, T4 DNA ligase, E. coli ligase, thermostable DNA ligases, and RNA ligases.

A stringent wash is performed following ligation, preferably including 0.1 N NaOH, such that noncovalently attached nucleic acid molecules are stripped off of a solid support. In this embodiment, the signal nucleic acid molecule preferably comprises a detectable label. The detection of the detectable label of the signal nucleic acid molecule on a solid support is indicitative of an exact match is sequence between an attached nucleic acid molecule and a nucleolytic activity-protected nucleic acid molecules of the present invention.

Treatment of Hybridized Complexes on Solid Support With Nucleolytic Activity

In another embodiment of the present invention (exemplified in FIG. 5), a further treatment with a nucleolytic activity is performed, in which after hybridization of nucleolytic activity-protected nucleic acid molecules are hybridized to attached nucleic acid molecules, the resulting attached nucleic acid molecule/nucleolytic activity-protected complexes are treated with a nucleolytic activity on the solid support.

In this embodiment the attached nucleic acid preferably includes a detectable label, and can include one or more nucleolytic activity-resistant linkages.

Preferably, nucleolytic activity-resistant linkages of attached nucleic acid molecules occur in portions of the nucleic acid molecule that are proximal to the solid support, such that a short segment of the sequence of an attached nucleic acid molecules (for example, 10 nucleotides or less in length) will not be cleaved by a nucleolytic activity when in the single-stranded state. Preferably, at least one of the nucleoside linkages in a probe nucleic acid molecule is sensitive to cleavage by a nucleolytic agent when the probe nucleic acid molecule or portion thereof is in the single stranded state, but is not sensitive to cleavage by a nucleolytic agent when the probe nucleic acid molecule is in the double stranded state, such as when hybridized to a complementary or substantially complementary nucleic acid molecule. As used herein, the single-stranded state can include one or more mismatched nucleotides that are not base-paired in a nucleic acid molecule that is base-paired in other regions. Preferably the detectable label is incorporated into that portion of the attached nucleic acid molecule that comprises nucleolytic activity sensitive linkages, and is not proximal to the solid support.

In the alternative, the attached nucleic acid molecule can be bound to the solid support indirectly, such as through a linker arm, and may or may not comprise nuclease-resistant linkages. Preferably, at least one of the nucleoside linkages in a probe nucleic acid molecule is sensitive to cleavage by a nucleolytic agent when the probe nucleic acid molecule or portion thereof is in the single stranded state, but is not sensitive to cleavage by a nucleolytic agent when the probe nucleic acid molecule is in the double stranded state, such as when hybridized to a complementary or substantially complementary nucleic acid molecule. Preferably a detectable label is incorporated into that portion of the attached nucleic acid molecule that comprises nucleolytic activity-sensitive linkages.

Thus, in this embodiment, following hybridization of the nucleolytic activity-protected nucleic acid molecules to the attached nucleic acid molecules on the solid support, the attached nucleic acid molecule/nucleolytic activity-protected complexes on the solid support are treated with a nucleolytic activity, such that portions of attached nucleic acid molecules that comprise one or more detectable labels and that are not hybridized to nucleolytic activity-protected nucleic acid molecules are cleaved, and the label is released from the solid support. Attached nucleic acid molecules that comprise one or more detectable labels and that are hybridized to nucleolytic activity-protected nucleic acids remain on the solid support, and can be detected by any of the methods described below.

Detection of Hybridized Complexes on Solid Support

Detection of hybridized complexes can be accomplished through any of several methods, including, but not limited to, spectrophotometric fluorescence detection, spectrophotometric absorption measurement, scintillation counting, autoradiography, phosphorimaging, light emission measurement, mass spectrometry, and the like.

Where the label on the target nucleic acid is not directly detectable, one then contacts the solid support, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g. by washing. The specific wash conditions employed will necessarily depend on the specific nature of the signal producing system that is employed, and will be known to those of skill in the art familiar with the particular signal producing system employed.

In detecting or visualizing the hybridization pattern, the intensity or signal value of the label can preferably be not only detected but quantified, by which is meant that the signal from each spot of the hybridization can be measured and compared to a unit value corresponding the signal emitted by known number of end labeled target nucleic acids to obtain a count or absolute value of the copy number of each end-labeled target that is hybridized to a particular spot on the array in the hybridization pattern.

Following detection or visualization, the hybridization pattern can be used to determine quantitative information about the genetic profile of the labeled target nucleic acid sample that was contacted with the array to generate the hybridization pattern, as well as the physiological source from which the labeled target nucleic acid sample was derived. By genetic profile is meant information regarding the types of nucleic acids present in the sample, e.g. in terms of the types of genes to which they are complementary, as well as the copy number of each particular nucleic acid in the sample. From this data, one can also derive information about the physiological source from which the target nucleic acid sample was derived, such as the types of genes expressed in the tissue or cell which is the physiological source, as well as the levels of expression of each gene, particularly in quantitative terms. Where target nucleic acids from two or more physiological sources are compared, the hybridization patterns may be compared to identify differences between the patterns. Where arrays in which each of the attached nucleic acid molecules corresponds to a known gene are employed, any discrepancies can be related to a differential expression of a particular gene in the physiological sources being compared. Thus, the present invention is useful in differential gene expression assays, where one may use the methods of the present invention in the differential expression analysis of: (a) diseased and normal tissue, e.g. neoplastic and normal tissue, (b) different tissue or subtissue types; and the like.

Comparing Expressed Nucleic Acid Molecules in Two Survey Populations

One embodiment of the present invention includes comparing expressed nucleic acid molecules from two survey populations of nucleic acid molecules. The survey populations are preferably related, but this need not be the case. For example, the first population may be of RNA isolated from a particular cell type that is cancerous, and the second population can be of RNA isolated from the same cell type that is not cancerous.

The method includes: contacting a first set of at least one probe nucleic acid molecule with a first survey population of nucleic acid molecules under conditions that promote hybridization between complementary nucleic acid molecules to generate a first probe-survey population mixture of nucleic acid molecules, contacting a second set of at least one probe nucleic acid molecule with a second survey population of nucleic acid molecules under conditions that promote hybridization between complementary nucleic acid molecules to generate a second probe-survey population mixture of nucleic acid molecules, treating the probe-survey population mixtures of nucleic acid molecules with one or more nucleolytic activities, such that single-stranded nucleic acid molecules are digested, to generate two populations of nucleolytic activity-protected nucleic acid molecules; contacting the two populations of nucleolytic activity-protected nucleic acid molecules with a solid support comprising one or more attached nucleic acid molecules under conditions that promote hybridization between nucleic acid molecules to generate attached nucleic acid molecule/nucleolytic activity-protected nucleic acid molecule complexes; and identifying one or more of said attached nucleic acid molecules or one or more of said nucleolytic activity-protected nucleic acid molecules in one or more attached nucleic acid molecule/nucleolytic activity-protected nucleic acid molecule complexes.

Preferably the first and second sets of probe nucleic acids comprise probe nucleic acids that are identical in sequence composition, but this need not be the case. Preferably, the first set of probe nucleic acids comprises a first detectable label and the second set of probe nucleic acids comprises a second detectable label, wherein the first and second detectable labels are distinguishable. In this case, the first and second sets of probe nucleic acid molecules are preferably at least partially complementary, or at least partially substantially complementary, to one or more attached nucleic acid molecules. For example, a survey population of RNA isolated from primary glial cells can be hybridized with a first probe set that is labeled with Cy3, and a survey population of RNA isolated from glioblastoma biopsy tissue can be hybridized with a second probe set that is labeled with Cy5. Following nuclease treatment of both probe-survey population mixtures, the nucleolytic activity-protected nucleic acid molecules from both as hybridizations are hybridized to a DNA array comprising attached nucleic acid molecules. Spectrophotometric scanning of the array reveals the level of expression of genes corresponding to the attached nucleic acid molecules by both populations.

For expression profiling, the survey population is preferably RNA, where the RNA can be total RNA or polyA+ RNA. The RNA is preferably isolated from at least one cell or tissue. Methods of RNA isolation are well known in the art (see, for example, Ausubel et al. (1998) *Current Protocols in Molecular Biology*, John Wiley and Sons). The survey population can also be amplified RNA, or RNA transcribed in vitro from one or more DNA templates. Methods of amplifying RNA and methods of in vitro transcription are also known in the arts If the survey population for expression profiling is DNA, it can be cDNA obtained from reverse transcription of RNA. Such cDNAs can be amplified. If amplified, preferably the amplification of DNA of the survey population is linear or substantially linear.

II. Compositions for Identifying Nucleic Acid Molecules

The present invention includes a composition including at least two probe nucleic acid molecules, and at least one solid support comprising at least two attached nucleic acid molecules. Preferably, a majority of the attached nucleic acid molecules are at least partially complementary or at least partially substantially complementary, or at least partially identical, or at least partially substantially identical to at least one probe nucleic acid molecule. The composition can comprise other components as well, such as, but not limited to, one or more of polymerases, nucleases, buffers, reagents, nucleotides, and additional sets of nucleic acid molecules. Components of the composition can optionally be provided in single or multiple containers.

Such compositions can be in the form of kits for carrying out the subject invention, where such kits at least include one or more probe nucleic acid molecules and at least one solid support comprising at least one attached nucleic acid molecule as described above and instructional material for carrying out the subject methodology, where the instructional material could be present on a package insert, on one or more containers in kit and/or packaging associated with the kit.

EXAMPLES

I. Detection of RNA Complementary to a DNA Probe

A. Synthesis of RNA Survey Populations

Two survey populations of RNA are synthesized from the DNA template pWPY001, a plasmid carrying a gene encoding glutathione transferase protein (GST). A first RNA population is synthesized from pWPY001 using the SP6 RNA polymerase promoter, and a second RNA population is synthesized from pWPY001 using the T7 RNA polymerase promoter that is oriented in the opposite direction. Thus, the two RNA populations are complementary to one another, one RNA population comprising at least a portion of the sense strand encoding the GST protein, and the other RNA population comprising at least a portion of the antisense strand. Prior to transcription, one aliquot of pWPY001 DNA is linearized with restriction enzyme HindIII and another aliquot of pWPY001 DNA is linearized with restriction enzyme XbaI by incubating the DNA with the enzymes at 37 degress C. for two hours using restriction enzyme buffers provided by the manufacturer. Both enzymes are obtained from Promega (Madison, Wis.). Following restriction enzyme digestion, the digestion products are separated on a 1% agarose gel. After staining the gel with ethidium bromide, fluorescent DNA bands corresponding to the size of the linearized plasmid are excised with a scalpel and extracted from the agarose using a QIAquick Gel Extraction kit (Qiagen, Valencia, Calif.).

Two in vitro transcription reactions are performed using one microgram of linearized pWPY001 DNA in each and a transcription buffer provided by the manufacturer of the enzymes, 10 mM DTT, 0.5 mM rNTPs, 100 units of Rnase inhibitor, and 40 units of T7 RNA or 40 units of SP6 RNA polymerase. The reactions are incubated for two hours at 3 8 degress C., and then 5 microliters of Rnase-free Dnase is added to a concentration of one unit per microgram of template DNA to each reaction, and the reactions are incubated for 15 minutes at 37 degress C. to digest the template DNA.

The resulting RNA populations are purified by adding 350 microliters of high salt buffer (Qiagen, Valencia, Calif.) containing freshly added beta-mercaptoethanol (ten microliters is added to one milliliter of buffer) to each reaction. 250 microliters of ethanol is then added to the mixtures, and they are pipeted up and down several times before being applied to Rneasy mini spin columns positioned in collection tubes (Qiagen, Valencia, Calif.). The column-plus-collection tubes are centrifuged for 15 seconds at 8,000×g.

The Rneasy columns are then positioned in new collection tubes. 500 microliters of RPE buffer (Qiagen, Valencia, Calif.) is added and the column-plus-collection tubes are centrifuged an additional 15 seconds at 8,000×g to wash the column. Two addition washes are performed, again each using 500 microliters of RPE buffer, the first by centrifuging 15 seconds at 8,000×g, and the second by centrifuging two minutes at 13,000×g. The Rneasy columns are then positioned in new collection tubes and centrifuged for one minute at 13,000×g. The columns are transferred to new collection tubes and 30 microliters of Rnase-free water are pipeted onto the Rneasy membranes of the columns. The columns are centrifuged for one minute at 8,000×g to elute the RNAs which will be used as the survey populations of nucleic acid molecules.

B. Solution Hybridization of Survey Population RNAs to Probe and Treatment with Nuclease Two hybridizations are performed. In each hybridization, two microliters containing 0.1 microgram of one of the RNAs of the survey populations synthesized in Part I, above, is added to 1×Mung Bean nuclease buffer (Pharmacia Biotech) containing 5 nanomolar $TA_{37}$. $TA_{37}$ is a probe DNA nucleic acid molecule having the following sequence:

5'-CAT GTT GGG TGG TTG TCC AAA AGA GCG TGC AGA GAT T-3' (SEQ ID NO:1), and is complementary to a portion of the nucleic acid molecules that make up the survey population of RNA synthesized using SP6 RNA polymerase in Part I. $TA_{37}$ is identical to a portion of the nucleic acid molecules that make up the survey population of RNA synthesized using T7 RNA polymerase in part I. The RNAs and $T_{37}$ probe, in a final volume of 40 microliters, are allowed to hybridize by heating the solutions for ten minutes at 90 degress C. and then incubating them at 50 degress C. for 60 minutes.

Following the 50 degress C. incubation, 12 units of Mung Bean nuclease are added to each of the mixtures, and the mixtures are incubated for 30 minutes at 37 degress C. EDTA is then added to a final concentration of 10 millimolar to stop the reactions. The resulting solutions contain mixtures of nuclease-protected nucleic acid molecules.

C. Synthesis of DNA Array and Hybridization of Nuclease-protected Nucleic Acid Molecules to Array A DNA oligonucleotide with an amino terminus, "$NH_2$-$TA_{25}$", with the sequence $NH_2$-AAT CTC TGC ACG CTC TTT TGG ACA A-3' (SEQ ID NO:2) is synthesized commercially. $NH_2$-$TA_{25}$ is complementary to a portion of the $TA_{37}$ probe, such that all of $NH_2$-$TA_{25}$ is complementary to $TA_{37}$, and $TA_{37}$ is partially complementary to $NH_2$-TA25, having 12 bases at the 5' end that are not complementary to $NH_2$-$TA_{25}$.

A solution of 10 micromolar $NH_2$-$TA_{25}$ is spotted onto sectors of two glass slides that have surface modified carboxyl groups, and the slides are placed in a dry light-impermeable box for three days. The slides are then washed, first in 0.2% SDS for 2 minutes, then twice in $H_2O$ for one minute, then once in NaBH solution (0.2 grams of $NaBH_4$ in 80 mls of 25% ethanol), and finally in $H_2O$ for one minute.

Twenty-two microliters of mixture 1 of nuclease-protected nucleic acid molecules (in which T7 polymerase-synthesized RNA was mixed with the probe) is applied to the sectors of slide 1, and twenty-two microliters of mixture 2 of nuclease-protected nucleic acid molecules (in which SP6 polymerase-synthesized RNA was mixed with the probe) is applied to the sectors of slide 2. Then glass cover slips are placed over the sectors of the slides, and the slides are placed in a box. The box is closed tightly and incubated at 90 degress C. for 10 minutes, and then at 50 degress C. for 60 minutes. The slides are then washed in a solution of 1×SSC/ 0.1% SDS pre-warmed to 50 degress C. for 3 minutes, and then washed in a solution of 0.1×SSC/0.1% SDS pre-warmed to 50 degress C., again for 3 minutes. The slides are then rinsed in water for 3 minutes at room temperature.

For labeling hybridized complexes on the arrays, an extension solution is prepared that contains 1×Klenow buffer (Promega, Madison, Wis.); 83 micromolar each of dATP, dGTP, and dTTP; 66 micromolar of Cy5-dCTP; and 5 units of Klenow fragment of DNA polymerase I in a final volume of 90 microliters. Twenty-two and a half microliters of the extension solution is added to each sector of the two slides, and the slides are incubated at room temperature for 30 minutes. The slides are then washed for 10 minute in a solution of 1×SSC/0.1% SDS, for 10 minutes in a solution of 0.1×SSC/0.1% SDS, for 5 minutes in water, for 10 minute in a solution of 1×SSC/0.1% SDS, for 10 minutes in a solution of 0.1×SSC/0.1% SDS, and finally for 10 minutes in water. The slides are then dried.

D. Detection of Signal on Hybridized Arrays

The arrays are scanned using a GSI Scanarray 3000 according to protocols suggested by the manufacturer. The results show that the slide that was hybridized with the RNA derived from the SP6 polymerase transcription reaction has fluorescence, and therefore, the survey population derived from the SP6 polymerase transcription reaction is partially complementary to the probe nucleic acid molecule $TA_{37}$ (and partially identical to the attached nucleic acid molecule $NH_2$-$TA_{25}$). In contrast, no fluorescence is detected when the slide that was hybridized with the RNA derived from the T7 polymerase reaction is scanned, indicating that the survey population derived from the T7 RNA polymerase transcription reaction is not partially complementary or complementary to the probe nucleic acid molecule $TA_{37}$, (and is not partially identical or identical to the attached nucleic acid molecule $NH_2$-$TA_{25}$).

II. Detection of a SNP

A. Synthesis of DNA Survey Population

A DNA oligonucleotide with the sequence:
5'-AATCTCTGCACGCTCTTTTGGACAACCACCCA-ACATGTTGTGCTT-3' (SEQ ID NO:3), "L45" was purchased commercially.

B. Solution Hybridization of Survey Population DNA To Probe and Treatment with Nuclease A hybridization is performed in which two microliters (0.1 microgram)of L45 (the DNA survey population) is added to 1 Mung Bean nuclease buffer (Pharmacia Biotech) containing 5 nanomolar M37. M37 is a probe DNA nucleic acid molecule having the following sequence: 5'-CATGTTGGGTGGTTGTCCAAAAGAGCGTGCAGA-GATT-3' (SEQ ID NO:4), and is complementary to a portion of the oligonucleotide that makes up the survey population of DNA. The DNA survey population and M37 probe, in a final volume of 40 microliters, are allowed to hybridize by heating the solutions for ten minutes at 90 degress C. and then incubating them at 50 degress C. for 60 minutes.

Following the 50 degress C. incubation, 12 units of Mung Bean nuclease are added to the hybridization mixture, and the mixture is incubated for 30 minutes at 37 degress C. EDTA is then added to a final concentration of 10 millimolar to stop the reactions. The resulting solution contains a mixture of nuclease-protected nucleic acid molecules.

C. Synthesis of DNA Array and Hybridization of Nuclease-protected Nucleic Acid Molecules to Array Four DNA oligonucleotides having amino termini,
"$NH_2$-S25-A" with sequence $NH_2$-AATCTCTGCACGCTCTTTTGGACAA-3' (SEQ ID NO:5),
"$NH_2$-S25-C" with sequence $NH_2$-AATCTCTGCACGCTCTTTTGGACAC-3' (SEQ ID NO:6),
"$NH_2$-S25-G" with sequence $NH_2$-AATCTCTGCACGCTCTTGGACAG-3' (SEQ ID NO:7), and
"$NH_2$-S25-T" with the sequence $NH_2$-AATCTCTGCACGCTCTITTGGACAT-3' (SEQ ID NO:8), are purchased commercially.

"$NH_2$-S25-A", "$NH_2$-S25-C", "$NH_2$-S25-G", and "$NH_2$-S25-T" are identical to a portion of the L45 probe, and complementary to a portion of the survey DNA molecule M37, such that 24 of the 25 bases of each of "$NH_2$-S25-A", "$NH_2$-S25-C", "$NH_2$-S25-G", and "$NH_2$-S25-T" are complementary to the survey DNA molecule (the 3' terminal base varies among the four attached oligos).

Four solutions of 10 micromolar of one of "$NH_2$-S25-A", "$NH_2$-S25-C", "$NH_2$-S25-G", and "$NH_2$-S25-T" are spotted onto separate sectors of a glass slide that has surface modified carboxyl groups, and the slide is placed in a dry light-impermeable box for three days. The slide is then washed, first in 0.2% SDS for two minutes, then twice in $H_2O$ for one minute, then once in $NaBH_4$ solution (0.2 grams of $NaBH_4$ in 80 mls of 25% ethanol), and finally in $H_2O$ for one minute.

Twenty-two microliters of the mixture of nuclease-protected nucleic acid molecules is applied to each sector of the slide. Then glass cover slips are placed over the sectors of the slide, and the slide is placed in a box. The box is closed tightly and incubated at 90 degress C. for 10 minutes, and then at 50 degress C. for 60 minutes. The slide is then washed in a solution of 1×SSC/0.1% SDS pre-warmed to 50 degress C. for 3 minutes, and then washed in a solution of 0.1×SSC/0.1% SDS pre-warmed to 50 degress C., again for 3 minutes. The slide is then rinsed in water for 3 minutes at room temperature.

For labeling hybridized complexes on the arrays, an extension solution is prepared that contains 1×Taq polymerase buffer, and 50 micromolar each of dATP, dGTP, and dTTP; 50 micromolar of Cy5-dCTP; and 5 units of Taq polymerase in a final volume of 90 microliters. Twenty-two and a half microliters of the extension solution is added to each sector of the slide, and the slide is incubated at 68 degress C. for 5 minutes. The slide is then washed for 10 minutes in a solution of 1×SSC/0.1% SDS, for 10 minutes in a solution of 0.1×SSC/0.1% SDS, for 5 minutes in water, for 10 minute in a solution of 1×SSC/0.1% SDS, for 10 minutes in a solution of 0.1×SSC/0.1% SDS, and finally for 10 minutes in water. Finally, the slide is dried.

D. Detection of Signal on Hybridized Arrays

The array is scanned using a GSI Scanarray 3000 according to protocols suggested by the manufacturer. The results show that the sector of the slide that has attached nucleic acid molecule "$NH_2$-S25-A" gives a fluorescent signal and there is no fluorescent signal from the sectors of the slide that have attached nucleic acid molecules "$NH_2$-S25-C", "$NH_2$-S25-G", and "$NH_2$-S25T". This indicates that only the attached nucleic acid molecule with a terminal adenine (A) could incorporate the fluorescent label, so that it can be deduced that the survey population nucleic acid molecule had complementary base thymine (T) at that position. In this way, the SNP sequence in the survey population is identified.

All publications, including patent documents and scientific articles, referred to in this application, including any bibliography, are incorporated by reference in their entirety for all purposes to the same extent as if each individual publication were individually incorporated by reference.

All headings are for the convenience of the reader and should not be used to limit the meaning of the text that follows the heading, unless so specified.

BIBLIOGRAPHY

U.S. Pat. No. 3,687,808
U.S. Pat. No. 5,143,854
U.S. Pat. No. 5,242,974
U.S. Pat. No. 5,359,115
U.S. Pat. No. 5,384,261
U.S. Pat. No. 5,405,783
U.S. Pat. No. 5,412,087
U.S. Pat. No. 5,420,328
U.S. Pat. No. 5,424,186
U.S. Pat. No. 5,429,807
U.S. Pat. No. 5,436,327
U.S. Pat. No. 5,445,934
U.S. Pat. No. 5,472,672
U.S. Pat. No. 5,527,681
U.S. Pat. No. 5,529,756
U.S. Pat. No. 5,532,128
U.S. Pat. No. 5,545,531
U.S. Pat. No. 5,554,501
U.S. Pat. No. 5,556,752
U.S. Pat. No. 5,561,071
U.S. Pat. No. 5,571,639
U.S. Pat. No. 5,593,839
U.S. Pat. No. 5,599,695
U.S. Pat. No. 5,624,711
U.S. Pat. No. 5,658,734
U.S. Pat. No. 5,700,637
WO 95/21944
Alizadeh et al. Nature 403: 503–5110.
Arribas et al. (1999) Clin. Cancer Res. 5: 3454–9.
Ausubel et al. (1998) *Current Protocols in Molecular Biology*, John Wiley and Sons.
Beaucage and Iyer (1992) Tetrahedron 48: 2223–2311.
Beaucage and Iyer (1993) Tetrahedron 49: 6123–6194.
Debouck and Goodfellow (1999) Nature Genetics Suppl. 21: 48–50.
Duggan, et al. (1999) Nature Genetics Suppl. 21: 10–14.
Eckstein, F., ed. (1991) Oligonucleotides and Analogs, A Practical Approach IRL Press.
Englisch et al. (1991) Angewandte Chemie, International Edition, 30: 613.
Gait, M. J., ed. (1984) Oligonucleotide Synthesis, A Practical Approach, IRL Press.
Gerhold et al.(1999) Trends Biochem Sci. 24: 168–173.
Haines and Gillispie (1992) Biotechniques 12: 736–741.
Harlowe and Lane (1988) *Antibodies, a Laboratory Manual*, Cold Spring Harbor Press.
Haugland (1992) Molecular Probes Handbook of Fluorescent Probes and Research Chemicals, Molecular Probes, Inc., Eugene, Oreg.
Kroschwitz, J. I. ed. (1990) Concise Encyclopedia of Polymer Science and Engineering, John Wiley and Sons.
Lau et al. (1995) Anal. Biochem. 209: 360–366.
Martin (1995) Helv. Chim. Acta, 78: 486–504.
Pollack et al. (1999) Nature Genetics 23: 4146.
Rosenthal and Jones (1990) Nucleic Acids Res. 18: 3095.
Sambrook et al. (1989) *Molecular Cloning: A Laboratory Manual*, 2nd edition, Cold Spring Harbor Press, Cold Spring Harbor, N.Y.
Sinha and Striepeke (1991) in Oligonucleotides and Analogues: A Practical Approach, Eckstein, ed, IRL Oxford.
Sinha and Cook (1988) Nucleic Acids Res. 1988 16: 2659.
Smith et al. (1985) Nucleic Acids Res. 13: 2399.
Strauss and Jacobowitz (1995) Brain Res. Mol. Brain Res. 20: 229–239.
Tanner et al. (1995) Clin. Cancer Res. 1: 1455–61.
Thiesen et al. (1992) Tertahedron Letters 33:3036.
Walmsely and Patient (1994) Mol. Biotechnol. 1: 265–275.

What is claimed is:

1. A method of detecting a mutation or single nucleotide polymorphism (SNP), comprising:
   a) contacting one or more probes that comprise DNA with a survey population of RNA molecules under conditions that promote hybridization between complementary nucleic acid molecules to generate a probe-survey population mixture of nucleic acid molecules that comprises at least one of said one or more probes hybridized to one or more survey population RNA molecules, wherein said one or more probes are at least partially complementary to one or more RNA molecules known to be or suspected of being present in the survey population, further wherein terminal nucleotide of said one or more probes is a SNP or mutation;
   b) treating said probe-survey population mixture of nucleic acid molecules with at least one nuclease that digests single-stranded DNA molecules, such that non-base-paired deoxynucleotides are digested, to generate a population of nucleic acid molecules comprising one or more nuclease-protected probes;
   c) contacting said population of nucleic acid molecules comprising one or more nuclease-protected probes with a solid support that comprises one or more attached nucleic acid molecules under conditions that promote hybridization between complementary nucleic acid molecules, wherein said one or more attached nucleic acid molecules are at least partially complementary to said one or more probes, to generate one or more attached nucleic acid molecule/nuclease-protected probe complexes; and
   d) detecting at least one of said one or more attached nucleic acid molecule/probe complexes to detect said SNP or mutation.

2. The method of claim 1, wherein the terminal nucleotide is labeled.

3. The method of claim 2, wherein said label is a radioisotope, a fluorochrome, an enzyme, or a specific binding member.

4. The method of claim 3, wherein said label is a fluorochrome.

5. The method of claim 1, wherein said one or more probes are from 10 to 250 bases in length.

6. The method of claim 5, wherein said one or more probes have one or more nuclease-resistant linkages.

7. The method of claim 1, wherein said probes are two or more probe.

8. The method of claim 1, wherein said survey population of RNA molecules is isolated from at least one cell, at least one tissue, at least one biological sample, at least one organism, or at least one environmental sample.

9. The method of claim 8, wherein said survey population of RNA molecules is isolated from at least one biological sample or at least one environmental sample.

10. The method of claim 9, wherein said survey population of RNA molecules is isolated from at least one biological sample.

11. The method of claim 1, wherein said nuclease that digests single-stranded DNA is S1 nuclease, Mung Bean nuclease, or Exonuclease III.

12. The method of claim 1, wherein solid support comprises glass, silicon, nylon, one or more polymers, one more plastics; one or more ceramics, or one or more metals.

13. The method of claim 12, wherein said solid support is an array.

14. The method of claim 12, wherein said solid support is a paramagnetic particle.

15. The method of claim 1, wherein said one or more attached nucleic acid molecules are between 10 and 250 nucleotides in length.

16. The method of claim 15, wherein said one or more attached nucleic acid molecules comprised DNA or peptide nucleic acids.

17. The method of claim 13, wherein said attached nucleic acid molecules are two or more attached nucleic acid molecules.

18. A method of detecting at least one RNA molecule in a survey population of RNA molecules, comprising:
   a) contacting one or more probes that comprise DNA with a survey population of RNA molecules under conditions that promote hybridization between complementary nucleic acid molecules to generate a probe-survey population mixture of nucleic acid molecules that comprises one or more probes hybridized to one or more survey population RNA molecules;
   b) treating said probe-survey population mixture of nucleic acid molecules with a nuclease that digests single-stranded DNA molecules, to generate a population of nuclease-resistant nucleic acid molecules comprising one or more nuclease-protected probes hybridized to one or more survey population RNA molecules;
   c) contacting said population of nuclease-resistant nucleic acid molecules with a solid support comprising one or more attached nucleic acid molecules, wherein said one or more attached nucleic acid molecules are at least partially complementary to said one or more probes, under conditions that promote hybridization between complementary nucleic acid molecules, to generate one or more attached nucleic acid molecule/nuclease-protected probe complexes; wherein said one or more attached nucleic acid molecule/nuclease-protected probe complexes comprise single-stranded overhangs having a uniform number of bases;
   d) labeling said one or more attached nucleic acid molecule/nuclease-protected probe complexes using at least one polymerase and at least one labeled nucleotide; and
   e) detecting label incorporated into at least one of said one or more attached nucleic acid molecule/nuclease-protected probe complexes, thereby detecting one or more RNA molecules of a survey population of RNA molecules.

19. The method of claim 18, wherein said one or more probes are from 10 to 250 bases in length.

20. The method of claim 18, wherein said probes are more than one probe.

21. The method of claim 18, wherein said survey population of RNA molecules is isolated from at least one cell, at least one tissue, at least one biological sample, at least one organism, or at least one environmental sample.

22. The method of claim 21, wherein said survey population of RNA molecules is isolated from at least one biological sample.

23. The method of claim 18, wherein said nuclease that digests single-stranded DNA molecules is S1 nuclease, Mung Bean nuclease, or Exonuclease III.

24. The method of claim 18, wherein said solid support comprises glass, silicon, nylon, one or more polymers, one or more plastics, one or more ceramics, or one or more metals.

25. The method of claim 24, wherein said solid support is an array.

26. The method of claim 18, wherein said one or more attached nucleic acid molecules are from 10 to 250 nucleotides in length.

27. The method of claim 18, wherein said one or more attached nucleic acid molecules comprise DNA.

28. The method of claim 25, wherein said attached nucleic acid molecules are two or more attached nucleic acid molecules.

29. The method of claim 18, in which said at least one polymerase is one selected from the group consisting of T4 DNA polymerase, *T. aquaticus* polymerase, Klenow fragment, T7 RNA polymerase, DNA polymerase 1, and SP6 RNA polymerase.

30. The method of claim 18, wherein said at least one labeled nucleotide comprises a radiosotope, a fluorochrome, an enzyme, or a specific binding member.

31. The method of claim 30, wherein said at least one labeled nucleotide comprises a fluorochrome.

32. The method of claim 18, wherein said at least one labeled nucleotide is four labeled nucleotides.

* * * * *